United States Patent
Anelli et al.

(12) 
(10) Patent No.: US 6,342,598 B1
(45) Date of Patent: Jan. 29, 2002

(54) AMPHIPATIC POLYCARBOXYLIC CHELATES AND COMPLEXES WITH PARAMAGNETIC METALS AS MRI CONTRAST AGENTS

(75) Inventors: Pier Lucio Anelli, Milan; Luciano Lattuada, Bussero; Fulvio Uggeri, Codogno; Giovanna Lux, Milan; Michele Serleti, Pessano con Bornago; Milena Gabellini, Ornago; Hervé Tournier, Valleiry, all of (IT)

(73) Assignee: Bracco International B.V., Amsterdam (NL)

( * ) Notice: Subject to any disclaimer, the term of this patent is extended or adjusted under 35 U.S.C. 154(b) by 0 days.

(21) Appl. No.: 09/448,289

(22) Filed: Nov. 24, 1999

(30) Foreign Application Priority Data

Nov. 26, 1998 (EP) ............................................. 98203997

(51) Int. Cl.$^7$ ............................................. C07D 257/02
(52) U.S. Cl. ................... 540/474; 424/450; 424/9.365; 424/9.321; 564/152; 554/79; 556/13; 534/15
(58) Field of Search .................. 540/474; 564/152; 424/450, 9.365, 9.321; 554/79; 556/13; 534/15

(56) References Cited

U.S. PATENT DOCUMENTS

| | | | | |
|---|---|---|---|---|
| 5,277,895 A | * | 1/1994 | Platzek et al. ................. | 424/9 |
| 5,312,617 A | * | 5/1994 | Unger et al. .................... | 424/9 |
| 5,364,613 A | * | 11/1994 | Sieving et al. ................. | 424/9 |
| 5,466,438 A | * | 11/1995 | Unger et al. ............. | 424/936.5 |
| 5,512,294 A | * | 4/1996 | Li et al. ....................... | 424/450 |
| 6,149,890 A | * | 11/2000 | Uggeri et al. ............ | 424/9.263 |

FOREIGN PATENT DOCUMENTS

| | | |
|---|---|---|
| DE | 19507820 A1 | 8/1996 |
| DE | 19608278 A1 | 8/1997 |
| EP | 0485045 A2 | 5/1992 |
| EP | 0512661 A1 | 11/1992 |
| EP | 0872479 A1 | 10/1998 |
| WO | WO92/21017 | 11/1992 |
| WO | WO94/27977 | 12/1994 |
| WO | WO9528392 | 10/1995 |
| WO | WO95/28967 | 11/1995 |
| WO | WO94/32741 | 12/1995 |
| WO | WO96/11023 | 4/1996 |
| WO | WO96/26182 | 8/1996 |
| WO | WO97/00087 | 1/1997 |
| WO | WO98/05626 | 2/1998 |
| WO | WO98/20908 | 5/1998 |

OTHER PUBLICATIONS

Baker et al J. Org. Chem. 64 (1999) 2683–2689.*
Miyamoto et al, "Design and Preparation of Gadolinium . . . " Chemi. Pharm. Bull. vol. 45 No. 12, 12/97, pp 2043–2050.
Jasanada et al, "Synthesis of Amphiphilic Chelating Agents . . . " Tetrahedron lett. vol. 33 No. 39, 4/92, pp. 5745–5748.
Kabalka et al, "Gadolinium–Labeled Liposomes . . . " Magnetic Resonance in Medicine. vol. 19 No. 2, 6/91, pp. 406–415.
Adzamli et al, "Development of Phosphonate . . . " J. Med. Chem. vol. 32 No. 1, 1989, pp. 139–144.
Goto et al, "Effect of Reticuloendothelia l. . . " Chem. Pharm. Bull. vol. 39 No. 1, 1991, pp. 230–232.
Hnatowich et al, "Labeling Of Preformed Liposomes . . . " J. Nuclear Medicine. vol. 22 No. 9, 1981, pp. 810–814.
Anelll et al, "L–Glutamic Acid And L–Lysine . . . " Bioconjugate Chem. vol. 10 No. 1, 1999, pp. 137–140, Etc.).

* cited by examiner

Primary Examiner—Richard L. Raymond
Assistant Examiner—Kahsay Habte
(74) Attorney, Agent, or Firm—Nixon & Vanderhye

(57) ABSTRACT

Substituted polycarboxylic ligand molecules and corresponding metal complexes of said ligands, preferably paramagnetic metals complexes for generating responses in the field of magnetic resonance imaging (MRI). The paramagnetic complexes of the polycarboxylic ligands possess advantageous tensioactive properties and are useful as MRI contrast media in formulations for investigating the blood pool.

8 Claims, No Drawings

AMPHIPATIC POLYCARBOXYLIC CHELATES AND COMPLEXES WITH PARAMAGNETIC METALS AS MRI CONTRAST AGENTS

FIELD OF THE INVENTION

The present invention addresses novel polycarboxylic ligand molecules and chelated complexes of said ligands with metals; the metals are for instance transition metals, e.g. paramagnetic metals for generating responses in the field of magnetic resonance imaging (MRI).

The present polycarboxylic ligands exhibit outstanding tensioactive properties which make them particularly useful in the form of paramagnetic chelates for making formulations and compositions useful as MRI contrast media of controllable and long lasting activity in the blood pool.

BACKGROUND ART

U.S. Pat. No. 5,466,438 (WO 92/231017) discloses compounds of formulae

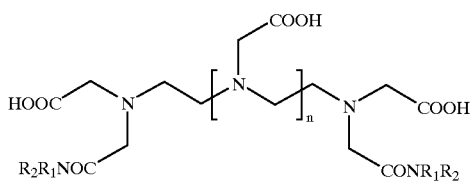

(I)

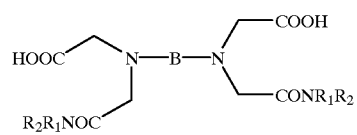

(II)

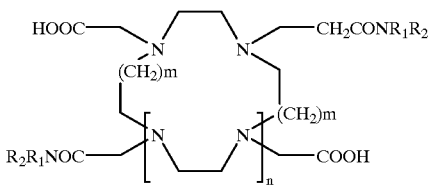

(III)

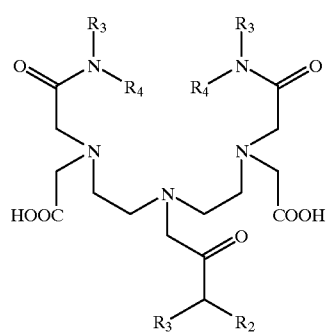

(IV)

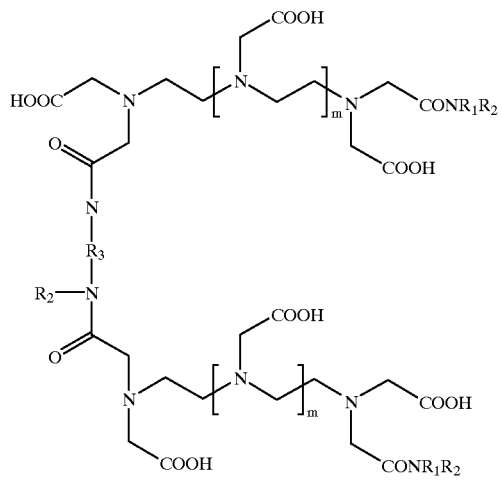

(V)

in which formulae I–III:
$R_1$ is independently a substituted or unsubstituted $C_{7-30}$ straight chain or cyclic compound;
$R_2$ is independently a substituted or unsubstituted $C_1$–$C_{30}$ straight chain or cyclic compound which may be internally interrupted by O, NH, $NR_3$ or S, where $R_3$ is a $C_1$–$C_3$ alkyl;
n is 0–1 in formula I and 1–20 in formula III;
m is 1–2;
B is a substituted or unsubstituted $C_1$–$C_{30}$ straight chain or cyclic compound which may be internally interrupted by O, NH, $NR_3$ or S.
In formula IV:
$R_1$, $R_2$ are independently H or a substituted or unsubstituted $C_7$–$C_{30}$ straight chain or cyclic compound;
$R_3$, $R_4$ are independently H or a substituted or unsubstituted $C_1$–$C_{30}$ straight chain or cyclic compound which may be internally interrupted by O, NH, $NR_5$ or S, where $R_5$ is a $C_1$–$C_3$ alkyl;
and in formula V:
$R_1$ is independently a substituted or unsubstituted $C_7$–$C_{30}$ straight chain or cyclic compound
$R_2$ is independently a substituted or unsubstituted $C_1$–$C_{30}$ straight chain or cyclic compound which may be internally interrupted by O, NH, $NR_4$ or S, where $R_4$ is a $C_1$–$C_3$ alkyl;
$R_3$ is independently a substituted or unsubstituted $C_1$–$C_{30}$ straight chain or cyclic compound which may be internally interrupted by O, NH, $NR_4$ or S, where $R_4$ is a $C_1$–$C_3$ alkyl and
m is 0–12.
The reference also discloses contrast agents obtained with the compounds of the above formulae (I–V), the latter further comprising lipids; the lipids are in the form of emulsions, liposomes or micelles.

U.S. Pat. No. 5,312,617 dicloses a method of imaging comprising administering to patients a contrast agent comprising a complex of a paramagnetic metal and a ligand selected from formulae IV and V disclosed in the foregoing U.S. Pat. No. 5,466,438.

Liposomes incorporating the above chelates are also disclosed as well as the possibility of having the compounds in the form of emulsions or micelles.

The micelles can be prepared by a variety of conventional liposome preparatory techniques; suitable lipids include, for example, monomyristoyl-phosphatidyl-choline, monopalmitoyl-phosphatidylcholine, dibutyroyl-phosphatidylcholine and the like, linoleic acid, oleic acid, palmitic acid, and the like.

Lipid emulsions can be prepared by conventional techniques, for instance a typical method is as follows:

1. In a suitable flask, the lipids are dissolved in ethanol or chloroform or any other suitable organic solvent.
2. The solvent is evaporated leaving a thin layer of lipid at the bottom of the flask.
3. The lipids are resuspended in an aqueous medium, such as phosphate buffered saline, this producing an emulsion.
4. Sonication or microfluidization can then be applied to improve homogeneity.
5. The contrast agents can be added to the lipids during preparation of the emulsion, or they may be added to the emulsion afterwards.
6. Useful additives include, for example, soybean lecithin, glucose, Pluronic F-68 and D,L-α-tocopherol; these additives are particularly useful where injectable intravenous formulations are desired.

The foregoing contrast agents may further comprise suspension stabilizers such as polyethyleneglycol, lactose, mannitol, sorbitol, ethyl alcohol, glycerin, lecithin, polyoxyethylene sorbitan monooleate, sorbitan monoleate and albumin. Various sugars and other polymers may also be added, such as polyethylene glycol, polyvinylpyrrolidone, polypropylene glycol and polyoxyethylene.

The contrast agents of this reference have high $T_1$ and $T_2$ relaxivity, especially when lipids are also present. Because of the high relaxivity, these contrast media are particularly useful for imaging the blood pool.

SUMMARY OF THE INVENTION

Despite the merit of the paramagnetic polycarboxylic chelates of the prior art as contrast agents for MRI, there was a need for a new range of chelating compounds of further improved properties designed to provide blood-pool contrast agents of outstanding long life in the circulation. In view of their structure including strongly hydrophobic and hydrophilic moieties, the compounds of the present invention achieve a significant step in the right direction.

The novel compounds of the present invention, either racemaic or enantiomeric have the following formulae (†) and (IV)

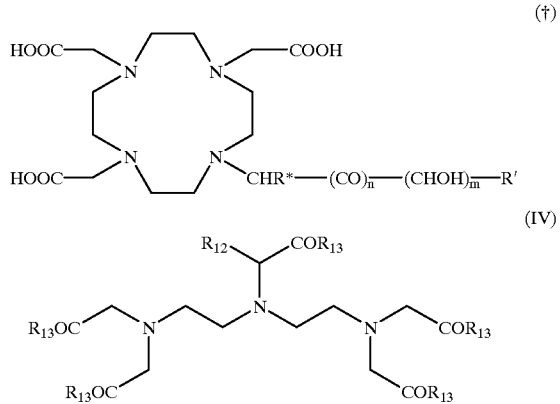

in which n and m are 1 or 0 but not simultaneously 1, and
when n=m=0, R' is H, and R* is a $C_{12-25}$ linear or ramified, saturated or unsaturated, hydrocarbon radical;
when n=1 and m=0, R* is H or a $C_{1-3}$ alkyl or alkylene substituent; and R' is selected from —$NHR_3$, —$NR_4R_5$ and —$OR_6$ where the $R_3$ to $R_6$ are independently $C_{1-25}$ linear or ramified, saturated or unsaturated, hydrocarbon radicals optionally interrupted by —CO— and/or —O— and optionally terminated by —$NR_7R_8$ in which $R_7$ and $R_8$ are independently H or $C_{12-25}$ hydrocarbon radicals;
when n=0 and m=1, R* is H or a $C_{1-3}$ alkyl or alkylene substituent; and R' is selected from $R_9$ and —$CH_2$—O—CO—$R_9$ in which $R_9$ is a $C_{10-30}$ linear or ramified, saturated or unsaturated, hydrocarbon radical optionally interrupted by —NH—, —$NR_{10}$—, —CO— or —O—, $R_{10}$ being a lower aliphatic hydrocarbon; and $R_{12}$ is H or a $C_{12-30}$ hydrocarbon radical optionally interrupted by —NH—, —$NR_{10}$—, —CO— or —O— and optionally terminated by a cholesteryl residue, and the $R_{13}$ are —OH; or one or two $R_{13}$ are a —NH—$R_{14}$ group in which $R_{14}$ is a $C_{2-30}$ linear or ramified, saturated or unsaturated, hydrocarbon radical optionally interrupted by —NH—, —$NR_{10}$—, —CO—, —O—, and/or —OPO(OH)O—, the remaining $R_{13}$ being —OH.

The compounds of formulae (†) and (IV) can be used as chelates of paramagnetic metals, preferably Gd(III), Mn(II), Cr(III), Cu(II), Fe(III), Pr(III), Nd(III), Sm(III), Tb(III), Yb(III), Dy(III), Ho(III) and Er(III) in the preparation of MRI contrast formulations and compositions of outstanding long life in the blood which makes them ideal agents for investigating the circulation in appended organs.

DETAILED DESCRIPTION OF THE INVENTION

Preferred are the compounds encompassed by formula (†), in which n and m are 1 or 0 but not simultaneously 1, and when n=1 and m=0, R* is an alkylene group, and the other variable groups are the meanings defined above.

Equally preferred are the compounds encompassed by formula (†), in which n and m are 1 or 0 but not simultaneously 1, and when n=1 and m=0, R* is H or a $C_{1-3}$ alkyl; and R' is selected from —$NHR_3$, or —$NR_4R_5$, where the $R_3$ to $R_5$ groups are independently $C_{12-25}$ linear or ramified, saturated or unsaturated, hydrocarbon radicals, optionally interrupted by —CO— and/or —O— and optionally terminated by —$NR_7R_8$ in which $R_7$ and $R_8$ are independently H or $C_{12-25}$ hydrocarbon radicals with the same meaning just above defined.

Equally preferred are the compounds encompassed by formula (†), in which n and m are 1 or 0 but not simultaneously 1, and when n=0 and m=1, R* is an alkylene group, and the other variable groups are the meaning defined above.

Equally preferred are the compounds encompassed by formula (†), in which n and m are 1 or 0 but not simultaneously 1, and when n=1 and m=0, R* is H or a $C_{1-3}$ alkyl; and R' is selected from $R_9$ and —$CH_2$—O—CO—$R_9$ in which $R_9$ is a $C_{12-25}$ linear or ramified, saturated or unsaturated, hydrocarbon radical optionally interrupted by —NH—, —$NR_{10}$—, —CO— or —O—, $R_{10}$ being a $C_{1-4}$ linear or ramified, saturated or unsaturated, hydrocarbon radical.

Furthermore the preferred compounds are of general formula (IV) in which $R_{12}$ is H, and two $R_{13}$ are a —NH—$R_{14}$ group in which $R_{14}$ is a $C_{12-25}$ linear or branched, saturated or unsaturated, hydrocarbon radical optionally interupted by —NH—, —$NR_{10}$—, —CO—, —O—, and/or —OPO(OH)O—, the remaining $R_{13}$ being —OH.

The compounds of formula (†) are preferably selected among compounds of the following formulae (I), (II) or (III)

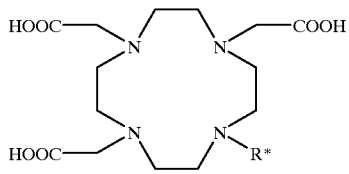

(I)

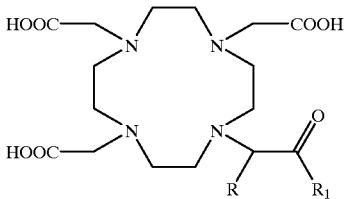

(II)

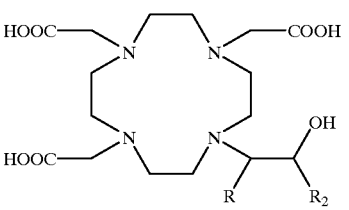

(III)

wherein R* is as defined heretofore;

R is H or a $C_{1-3}$ alkyl or alkylene substituent;

$R_1$ is selected from —$NHR_3$, —$NR_4R_5$ and —$OR_6$ where the $R_3$ to $R_6$ are independently $C_{1-25}$ linear or ramified, saturated or unsaturated, hydrocarbon radicals optionally interrupted by —CO— and/or —O— and optionally terminated by —$NR_7R_8$ in which $R_7$ and $R_8$ are independently H or $C_{12-25}$ hydrocarbon radicals;

$R_2$ is selected from $R_9$ and —$CH_2$—O—CO—$R_9$ in which $R_9$ is a $C_{10-60}$ linear or ramified, saturated or unsaturated, hydrocarbon radical optionally interrupted by one or more —NH—, —$NR_{10}$—, —CO— or —O—, $R_{10}$ being a lower aliphatic hydrocarbon.

For instance, the compounds of formula (II) can have formula (IIa)

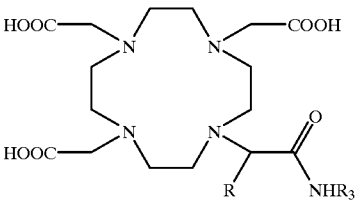

(IIa)

in which $R_3$ is a $C_{12-25}$ linear or ramified, saturated or unsaturated, hydrocarbon radical.

Particularly preferred are the compounds of formula (IIa) in which $R_3$ is a $C_{16-20}$ linear or ramified, saturated or unsaturated, hydrocarbon radical.

Or they can have formula (IIb)

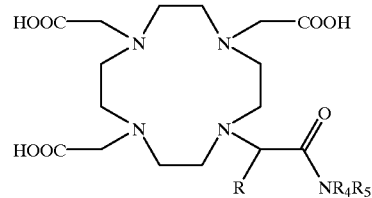

(IIb)

in which $R_4$ and $R_5$ are independently $C_{12-25}$ linear or ramified, saturated or unsaturated, hydrocarbon radicals optionally interrupted by —CO— and/or —O—.

Particularly preferred are the compounds of formula (IIb) in which $R_4$ and $R_5$ are independently $C_{16-20}$ linear or ramified, saturated or unsaturated, hydrocarbon radicals interrupted by —CO— and —O—.

Furthermore, they can have formula (IIc)

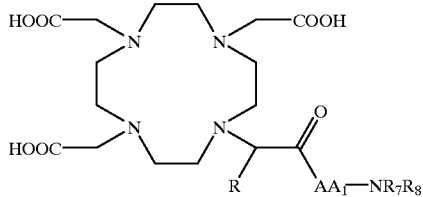

(IIc)

in which A is —NH— or —O—, $A_1$ is a $C_{1-20}$ linear or ramified, saturated or unsaturated, hydrocarbon radicals optionally interrupted by —CO— and/or —O— and $R_7$ and $R_8$ are defined as above.

Particularly preferred are the compounds of formula (IIc) in which R is an alkylene substituent.

Equally preferred are the compounds of formula (IIc) in which A is —NH—, $A_1$ is a $C_{1-20}$ linear or ramified, saturated or unsaturated, hydrocarbon radicals interrupted by —CO— and —O— and $R_7$ and $R_8$ are defined as above. Also the compounds of formula (IIc) are preferred in which A is —O— and $A_1$ is a $C_{1-20}$ linear or ramified, saturated or unsaturated, hydrocarbon radicals interrupted by —CO— and —O— and $R_7$ and $R_8$ are defined as above.

Compounds of formula (III) can have formula (IIIa)

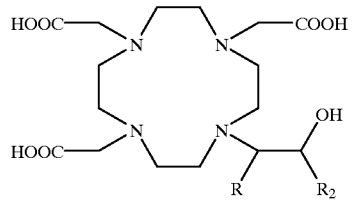

(IIIa)

in which R is H and $R_2$ is is a $C_{10-30}$ linear or ramified, saturated or unsaturated, hydrocarbon radical optionally interrupted by one or more —NH—, —N—, —CO— or —O. Otherwise, they can have formula (IIIb) below

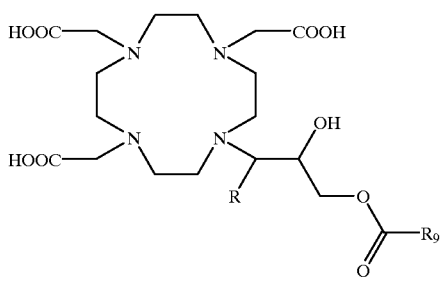

(IIIb)

in which R is H and $R_9$ is a $C_{10-25}$ linear alkyl, or a $C_{10-50}$ linear or ramified, saturated or unsaturated, hydrocarbon radical optionally interrupted by one or more —N—, —CO— and/or —O—.

Some preferred compounds of formula (IV) are those in which all the $R_{13}$ are —OH and $R_{12}$ is defined as mentioned above. Otherwise, compounds of formula (IV) can be selected from the compounds of formulae (IVa) and (IVb) below. In Formula (IVa),

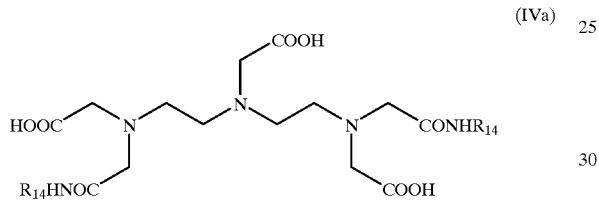

(IVa)

the $R_{14}$ are independently as defined above for formula (IV).

Particularly preferred are the compounds of formula (Iva) in which $R_{14}$ is $Cl_{2-25}$ linear or ramified, saturated or unsaturated, hydrocarbon radical optionally interrupted by —CO— and/or —O—, and/or —OPO(OH)O—.

In formula (IVb) shown below,

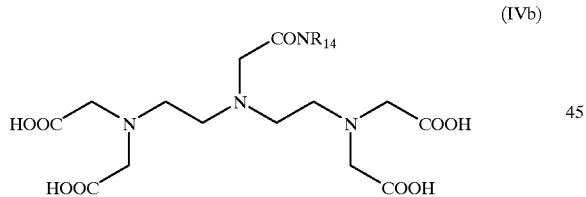

(IVb)

$R_{14}$ is a $C_{12-25}$ linear or ramified, saturated or unsaturated, hydrocarbon radical.

The compounds of this invention of formulae (†) and (IV) can be as represented in the formulae; or they can be in the form of complex chelates with paramagnetic metal ions (as indicated heretofore) and the salts thereof with physiologically acceptable bases selected from primary, secondary, tertiary amines and basic aminoacids, or inorganic hydroxides of sodium, potassium, magnesium, calcium or mixtures thereof;

or with physiologically acceptable anions of organic acids selected from acetate, succinate, citrate, fumarate, maleate, oxalate, or inorganic acids selected from hydrogen halides, sulphates, phosphates, phosphonates and the like;

or with cations or anions of aminoacids selected from lysine, arginine, ornithine, aspartic and glutamic acids, and the like;

For preparing the compounds of formula (I) in the form of complexes with metals (ME), one can proceed as in the following Scheme 1:

Scheme 1

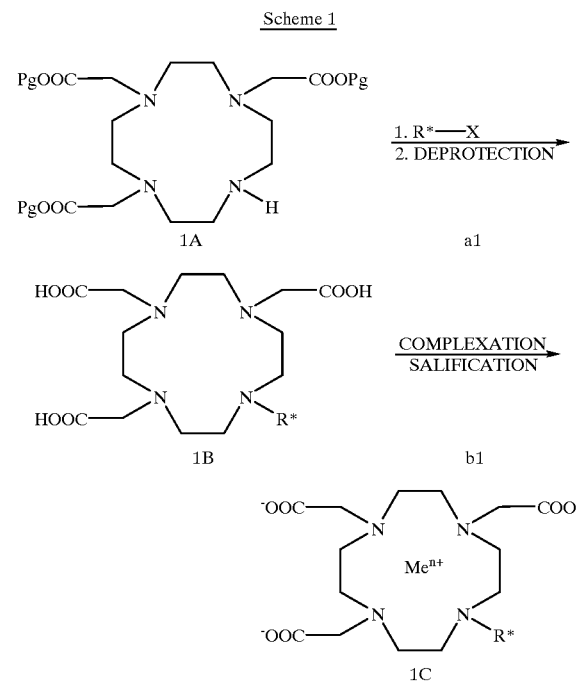

Where Pg is a protecting group;

R* is as defined for formula (I);

$ME^{n+}$ is a metal ion;

n=2 or 3.

In step a1 the compound 1A, i.e. 1,4,7,10-tetraazacyclododecane-1,4,7-triacetic acid, whose carboxylic groups are suitably protected by groups such as benzyl or t-butyl, is reacted with R*—X, where R* is a substituent residue and X is a leaving group such as Cl, Br, I. The reaction product is then deprotected by known methods (e.g. with $CF_3COOH$) to give the free ligand 1B. The ligand is then complexed with a suitable metal ion oxide or salt (preferably paramagnetic), such as Gd oxide, chloride or acetate, in order to obtain the desired metal complex chelate 1C. Depending on the value of n, 1C may be salified with a suitable counter-ion.

For the complexes of the compounds of formula (IIa), one may proceed according to the scheme 2 below:

Scheme 2

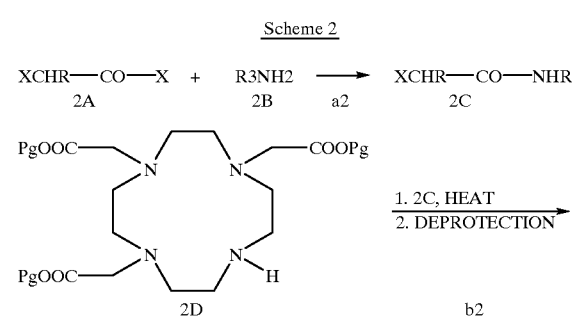

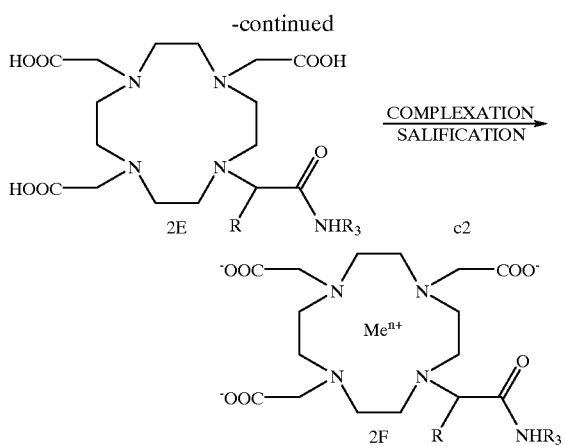

in which Pg is a protecting group as in Scheme 1;

R and $R_3$ have been defined above; and ME and n are as in Scheme 1.

According to the method of Scheme 2, one prepares compound 2C by the reaction of a halogenated halide (or equivalent) with a primary amine $R_3NH_2$ in a suitable solvent, such as $CH_2Cl_2$, $CHCl_3$ or $H_2O/CH_2Cl_2$ mixtures, in the presence of a base (e.g. $K_2CO_3$). Then, Compound 2C is reacted with compound 2D and the product is deprotected (b2) to furnish the desired free ligand 2E. The latter is finally complexed according to the general procedure disclosed in Scheme 1. If required, i.e. depending on whether n has an appropriate value, compound 2F may be salified with a suitable counter-ion.

For preparing the metal complexes of the compounds of formula (IIb), one may proceed according to the Scheme 3 below:

Scheme 3

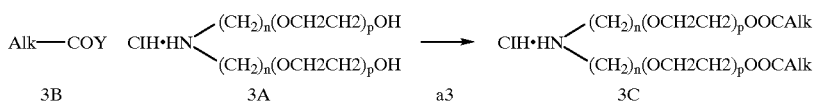

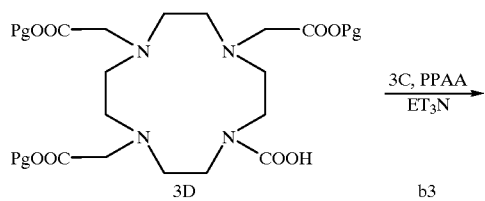

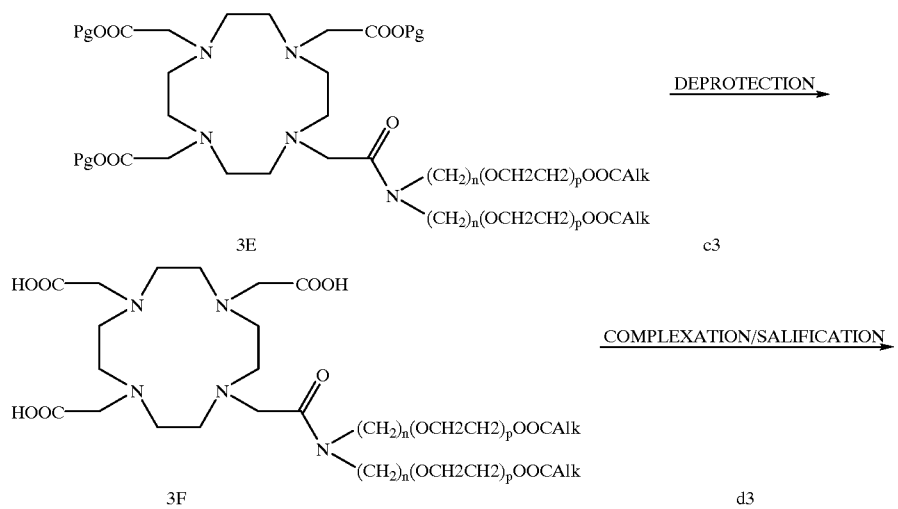

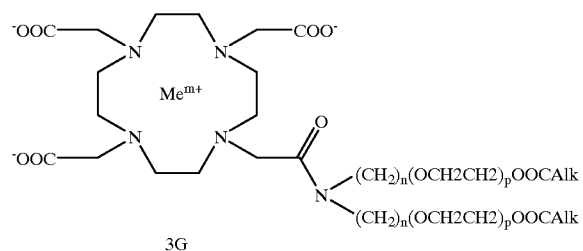

in which n=1–6; p=0–5; m=2 or 3; Y=halogen; Pg is a protecting group and Alk is a lipophilic alkyl chain.

In step a3 compound 3A is reacted with a suitable long-chain carboxylic acid halide 3B in a suitable aprotic dipolar solvent to obtain compound 3C. The latter is reacted (step b3) with compound 3D, i.e. 1,4,7,10-tetraazacyclododecane-1,4,7,10-tetraacetic acid of which three acetic groups are protected with, for example, benzyl or t-butyl groups, in the presence of 1-propanephosphonic acid cyclic anhydride (PPAA) and a base (e.g. Et$_3$N) in a suitable solvent such as CH$_2$Cl$_2$.

Compound 3E obtained in step c3 is deprotected by known methods (e.g. by catalytic hydrogenation) which provides the free ligand 3F, which is then complexed with a metal (step d3), according to the procedure described earlier.

This affords the desired complex chelate 3G. Then, compound 3G may be salified with a suitable counter-ion if the value of m permits.

For preparing the compounds of formula (IIc) in which A is —NH—, one can proceed like in the previous scheme, the first step (condensation of triprotected 1,4,7,10-tetraazacyclododecane-1,4,7,10-tetraacetic acid (4A) with an amine H$_2$N-A$_1$-NR$_7$R$_8$ (4B) being effected in the presence, as condensing a agent, of (benzotriazo-1-yloxy)-tris(dimethylamino)-phosphonium hexafluorophosphate and a sterically hindered tertiary amine such as diisopropylethylamine (DIEA) when 4B is an a-aminoacid derivative, or N,N'-bis(2-oxo-3-oxazolidyl)-phosphoro-diamidic chloride (BOP). This is illustrated in Scheme 4.

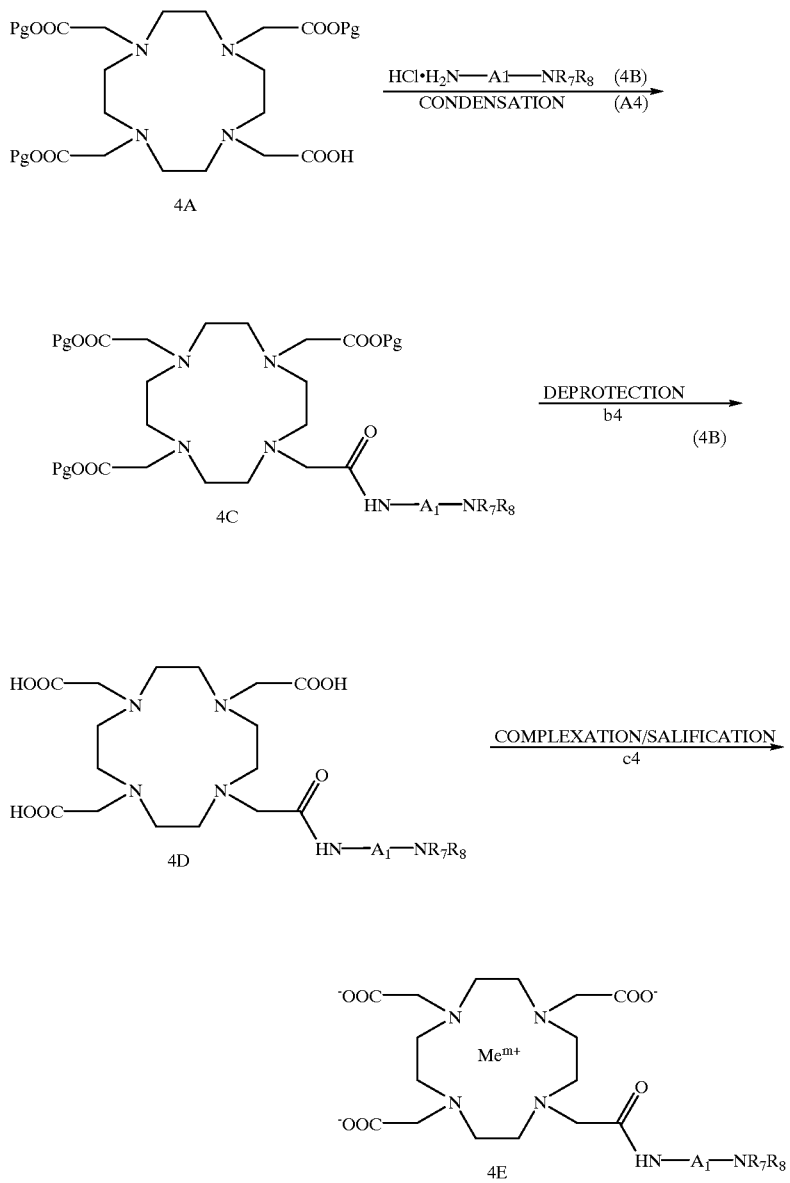

Scheme 4

A similar method can be applied for compounds (IIc) in which A is —O—, i.e. the esterification of triprotected 1,4,7,10-tetraazacyclododecane-1,4,7,10-tetraacetic acid with a halogenated compound X—A$_1$—NR$_7$R$_8$ in the presence of 1,8-diazabicyclo[5.4.0]undecene. Then the resulting intermediate 5C is deprotected, complexed and salified as in the previous schemes (Scheme 5).

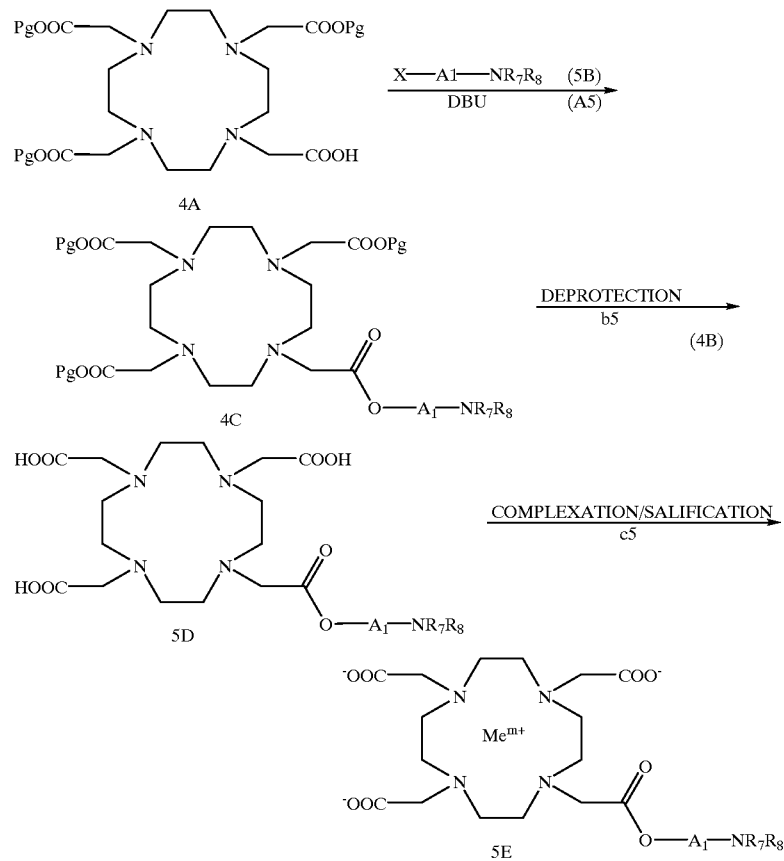

The compounds of formula (IIIa) can be obtained as illustrated in Scheme 6. The protected 1,4,7,10-tetraazacyclododecane-1,4,7-triacetic acid 6A is reacted with an alkyl epoxide

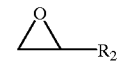

in a solvent such as ethanol and the resulting product is deprotected and treated as described in the previous schemes

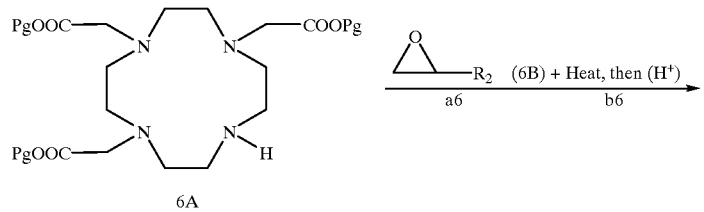

-continued

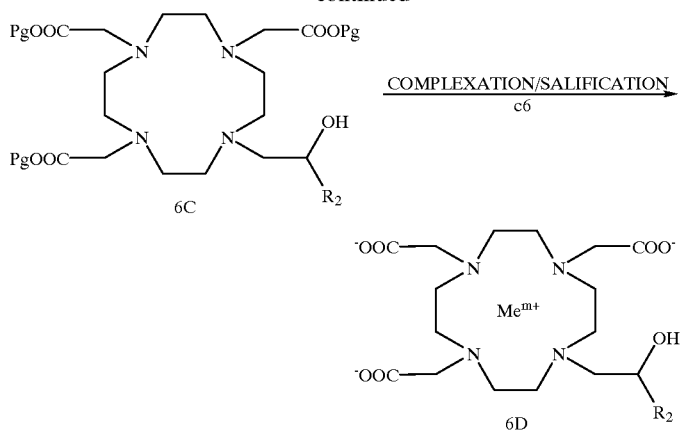

A possible technique for making the compounds (IIIb) and the corresponding metal chelates and salts is illustrated in Scheme 7. Here the initial reactant to be condensed with the triprotected 1,4,7,10-tetraaza-cyclododecane-1,4,7-triacetic acid is 2,3-epoxypropanol 7B which provides the vic-diol 7C, the primary —OH of which is thereafter esterified with an acid $R_9$-COOH, the remaining steps being as described previously.

Scheme 7

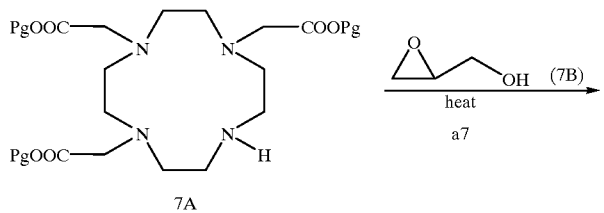

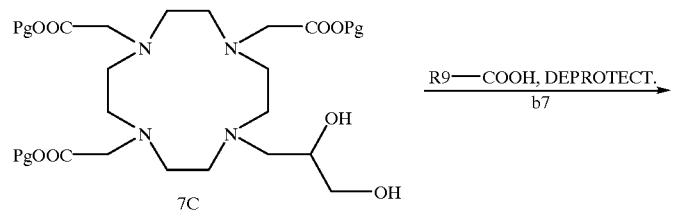

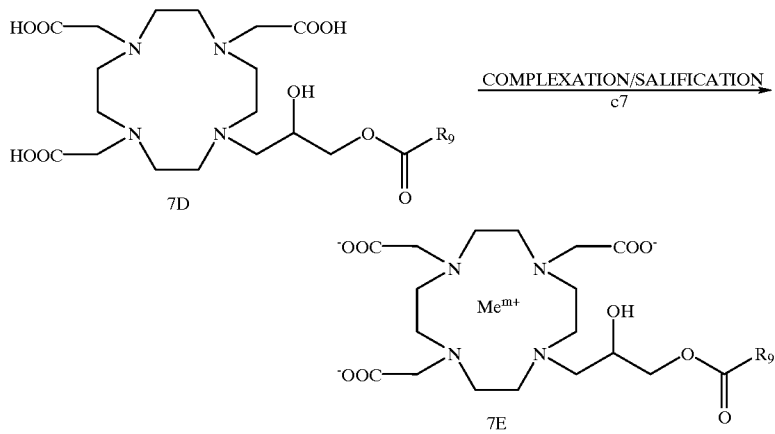

The following preparative methods are applicable regarding the compounds of formula (IV) in which $R_{12}$ is H. For instance, for the compounds (IVa), one may operate as illustrated in Scheme 8, by reacting in DMF the DTPA cyclic, dianhydride (N,N-bis[2-(2,6-dioxo-4-morpholinyl) ethyl]gly-cine) 8A with an amine $H_2NR_{14}$, the remaining step being that of complexation with a metal and possible salification as discussed earlier.

Scheme 8

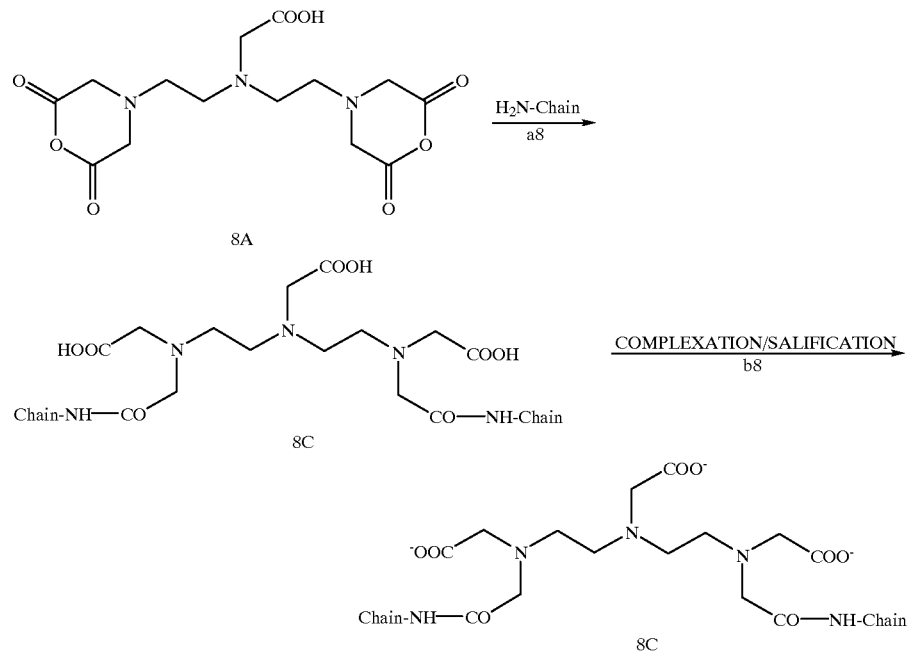

Otherwise, one may first effect protection of up to four of the —COOH's groups in DTPA, the unprotected group being thereafter amidated in DMF with an amine $H_2NR_{14}$ according to usual means (see Scheme 9).

Scheme 9

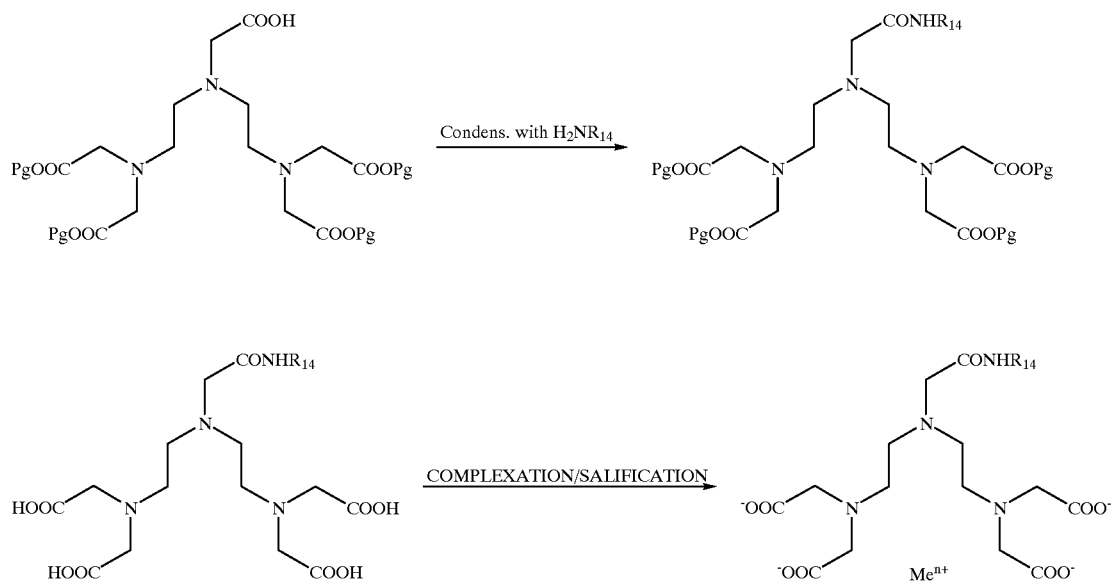

One preparative route for the compounds of formula (IV) with a substituent $R_{12}$ in α- to the central carboxylic function is to first attach in the said position, a carbon chain functionalized with, for example, a —$NH_2$ or —COOH group (Scheme 10). For example, compound 10A can be prepared, according to Rapoport et al. in J. Org. Chem. 58 (1993), 1151–1158, or using a method disclosed in WO 98/05626. The synthon is then reacted with, for example, a chloride of a carboxylic acid having the desired chain length, or with a suitable amine, depending on the nature of the said functional group. Then, the resulting compound 10B is deprotected and complexed as already shown in the previous Schemes.

phosphatidic acid (PA), phosphatidylcholine (PC), phosphatidylethanolamine (PE), phosphatidylserine (PS), phosphatidylglycerol (PG), phosphatidylinositol (PI), cardiolipin (CL) and sphyngomielin (SM). The amphipatic compound may also consists of a monophosphate ester of a substituted or partially substituted glycerol, at least one functional group of said glycerol being esterified by saturated or unsaturated aliphatic fatty acid, or etherified by saturated or unsaturated alcohol, the other two acidic functions of the phosphoric acid being either free or salified with alkali or earth-alkali metals. Preferably the phosphate esters will include monophosphates of fatty acid glycerides selected from dimiristoylphosphatidic acid, dipalmitoylphosphatidic acid, or distearoylphosphatidic acid.

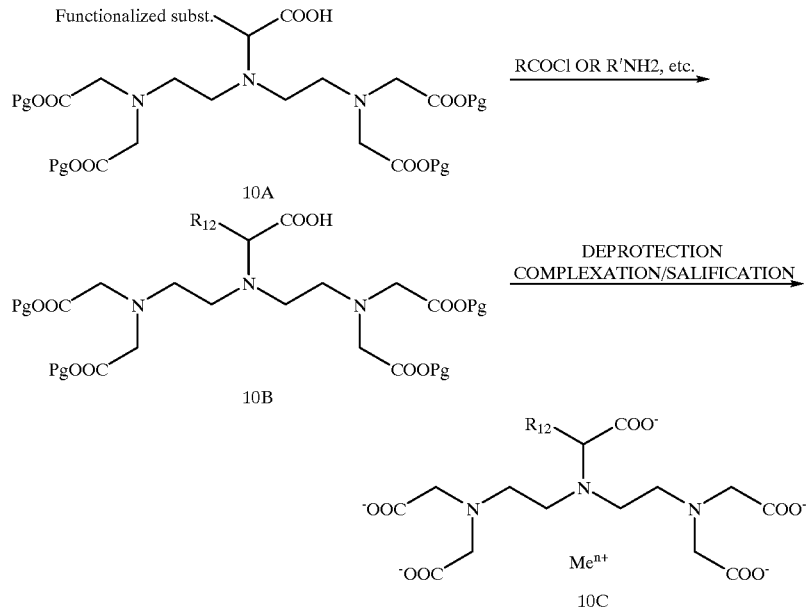

Scheme 10

This technique is exemplified in the synthesis of the compound of Example 16 involving reaction with cholesteryl chloroformate.

The injectable compositions and formulations according to the invention which are usable as contrast agents for MRI investigations will preferably contain further additives, in addition to one or more of the afore discussed novel paramagnetic chelates and a carrier liquid. The additives include non-ionic and/or ionic surfactants and mixtures thereof, as well as other amphipatic compounds. Due to their physiological suitability, the non-ionic surfactants are preferred. The non-ionic surfactants are preferably block-copolymers having polyoxyethylene and polyoxypropylene sequences, polyethyleneglycol-alkylethers such as, for example, polyethyleneglycol-octadecylether, or polyoxyethylene fatty acid esters or polyoxyethylene sorbitan fatty acid esters, or n-alkyl glycopyranoside and n-alkyl maltotrioside. The non-ionic surfactant in the compositions of the invention is conveniently selected from the commercially available products, such as Pluronic®, Poloxamer®, Poloxamine®, Synperonic®, BRIJ®, Myrj®, Tween®s (polysorbates) and their mixtures. The weight proportion of the surfactant relative to the amount of the paramagnetic imaging agent is from 1:50 to 50:1, preferably 1:10 to 10:1, and even more preferably 1:1. The ionic surfactants preferably include biliary acid salts such as sodium deoxycholate.

The amphipatic compounds suitable in the present compositions are phospholipids which may be selected from The phospholipids may also include diacyl and dialkyl glycerophospholipids in which the aliphatic chains have, at least twelve carbon atoms, as well as one or more compounds selected from ionic and neutral phospholipids, monoalkyl or alkenyl esters of phosphoric acid and/or cholesterol, ergosterol, phytosterol, sitosterol, lanosterol, tocopherol. In the compositions containing phospholipids, the weight proportion of the phospholipids to the amphiphilic chelate seems not critical and it may vary, for example, from 1:50 to 50:1. The practical range will be between 10:1 and 1:10, preferably between 1:5 and 5:1 and even more preferably between 1:3 and 3:1. In the compositions in which phospholipids are used the weight ratio of the phospholipid to the surfactant may vary as above, however the ranges from 1:10 to 10:1 and, preferably, between 1:2 and 2:1 are considered optimal.

The compositions of the present invention may exist in micellar form, in which case they can be prepared using known techniques, namely as described in WO 97/00087; Polym. Prepr. 1997, 38(1), 545–546; Acad. Radiol. 1996, 3, 232–238. These documents describe micelles of amphiphilic Gd chelates useful in percutaneous lymphography. The micelles have particle size between 10 and 500 nm, preferably between 50 and 200 nm.

The micelles can be prepared in any physiologically acceptable aqueous liquid carrier, such as water or saline, neat or bufferd, according to usual practice. Depending upon the choice of the components, the dispersion can be achieved by gentle mixing or by more energetic means, such as homogenisation, microfluidization or sonication.

In an advantageous mode of preparing the micelles of the invention, one part by weight of the paramagnetic chelate contrast component is admixed with one to two parts each of surfactants and of lipids, and with 100 to 200 parts of liquid carrier, for example Tris/Glycerol buffer.

The compositions can be stored and used as such, or may be lyophilized dry, according to known methods, e.g. by freeze-drying. This dry form (porous lumps or free flowing powder) is particularly convenient for long-term storage. The formulations can be reconstituted before usage by dispersion of the lyophilizate in a physiologically acceptable liquid carrier, thus obtaining a suspension corresponding to the early formulation and directly usable as NMR imaging contrast agent.

For practically applying the compositions of the invention in the medical field, the lyophilized components and the carrier liquid can be marketed separately in a kit form. The lyophilized components may be stored under a dry, inert atmosphere and the carrier liquid may further contain isotonic additives and other physiologically acceptable ingredients, such as various mineral salts, vitamins, etc.

The compositions of the invention are particularly useful as magnetic resonance contrast agents for the imaging of the blood pool. They have shown to possess a sufficiently high relaxivity effect on the blood after injection in the rat and an exceptionally favourable elimination kinetic profile from the blood circulation, as demonstrated by pharmacokinetic and biodistribution data. These two combined characteristics make them very suitable for angiographic magnetic resonance imaging in general. The compositions of the invention can therefore facilitate MR angiography and help to assess myocardial and cerebral ischemia, pulmonary embolism, vascularization of tumours and tumour perfusion.

The following examples further illustrate the invention in more detail.

EXAMPLE 1

[10-Hexadecyl-1,4,7,10-tetraazacyclododecane-1,4,7-triacetato(3-)]gadolinium

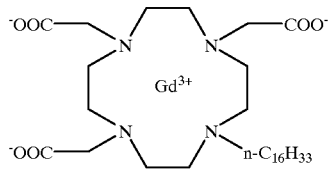

A) 10-Hexadecyl-1,4,7,10-tetraazacyclododecane-1,4,7-triacetic acid

A mixture of 1,4,7,10-tetraazacyclododecane-1,4,7-triacetic acid tris(1,1-dimethylethyl) ester (prepared according to EP-A-299795) (20.6 g; 40 mmol) and 1-bromohexadecane (12.4 g; 40.6 mmol) in $CH_3CN$ (500 mL) was heated to reflux for 2 h. Then, the reaction mixture was evaporated and the residue was flash chromatographed ($CH_2Cl_2$/MeOH=9/1 (v/v)) to give a solid. This product was dissolved in $CHCl_3$ and an excess $CF_3COOH$ was added. After 2 h the reaction mixture was evaporated and the oily residue redissolved in $CF_3COOH$. After 16 h at room temperature the solution was evaporated and the residue was purified by flash chromatography ($CH_2Cl_2$/MeOH/$NH_4OH$ 25% (w/w)=12/4/1 (v/v/v)). The product was dissolved in $H_2O$ and acidified with 6N HCl; the solution was loaded onto an Amberlite⌑ XAD-8 resin column and eluted with a $CH_3CN$/$H_2O$ gradient.

The fractions containing the product were evaporated and dried under reduced pressure to give the desired product (8.1 g; 14 mmol).

Yield 35%. HPLC: 98% (area %). Karl Fisher (K. F.): 4.05%. The $^{13}C$-NMR, MS and IR spectra were consistent with the structure.

| | Elemental analysis (%): | | | |
|---|---|---|---|---|
| | C | H | N | |
| Calcd. | 63.13 | 10.24 | 9.82 | |
| Found | 63.16 | 10.53 | 9.84 | anhydrous |

B) [10-Hexadecyl-1,4,7,10-tetraazacyclododecane-1,4,7-triacetato (3-)]gadolinium A solution of $GdCl_3.6H_2O$ (3.9 g; 10.5 mmol) in $H_2O$ (40 mL) was added to a solution of the product from the previous preparation (6 g; 10.5 mmol) in $H_2O$; the pH was maintained at 6.8 by addition of a solution of NaOH 1 N (30 mL). The solution was treated with n-BuOH and the organic phase was evaporated to give a solid that was extracted at reflux with $CHCl_3$ in a Soxhlet apparatus. The solution was evaporated to give a solid. The product was dissolved in H2O and i-PrOH, loaded onto a mixed bed of Amberlite⌑ IRA 400 (250 mL) and Duolite⌑ C20 MB resin (250 mL); then, it was and eluted with $H_2O$/i-PrOH 1:1. The fractions containing the product were evaporated to give the title compound (2 g; 2.7 mmol).Yield 26%.

HPLC: 99% (area %); K. F.: 2.49%; Weight loss: (120° C.): 10.45%. The MS and IR spectra were consistent with the structure postulated.

| | Elemental analysis (%): | | | |
|---|---|---|---|---|
| | C | H | N | Gd |
| Calcd. | 49.70 | 7.65 | 7.73 | 21.69 |
| Found | 49.80 | 7.95 | 7.69 | 21.49 |

EXAMPLE 2

[10-Octadecyl-1,4,7,10-tetraazacyclododecane-1,4,7-triacetato(3-)]gadolinium

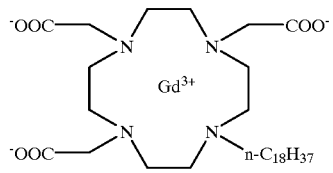

A) 10-Octadecyl-1,4,7,10-tetraazacyclododecane-1,4,7-triacetic acid

A mixture of 1,4,7,10-tetraazacyclododecane-1,4,7-triacetic acid tris(1,1-dimethylethyl) ester (37.5 g; 72.8 mmol) and 1-bromooctadecane (24.5 g; 73.5 mmol) in $CH_3CN$ (500 mL) was heated to reflux. After 2 h the reaction mixture was evaporated and the residue was dissolved in $CHCl_3$ and a portion of $CF_3COOH$ was added. After 16 h at room temperature the reaction mixture was evaporated and the oily residue dissolved in $CF_3COOH$. After 3 days at room temperature, the solution was evaporated, the residue taken up in $CHCl_3$ and the solution evaporated. This operation was repeated three times. The oily residue was purified by flash chromatography as follows:

Eluents: (a) $CH_2Cl_2$/MeOH=3/1 (v/v) 3 liters
(b) $CH_2Cl_2$/MeOH/$NH_4OH$ 25% (w/w)=12/4/1 (v/v/v) 12 liters (c) CH$_2$Cl$_2$/MeOH/NH$_4$OH 25% (w/w)=6/3/1 (v/v/v) 2 liters The product was dissolved in H$_2$O and acidified with 6N HCl; then, the solution was loaded onto an Amberlite® XAD-8 resin column and eluted with a CH$_3$CN/H$_2$O gradient. The product started eluting with 20% CH$_3$CN.

The fractions containing the product were evaporated and dried under reduced pressure to give the desired product (24.2 g; 40.4 mmol). Yield 55%.

HPLC: 91% (area %); K. F.: 8.01%; the $^{13}$C-NMR, MS and IR spectra were consistent with the structure.

| | Elemental analysis (%): | | | |
|---|---|---|---|---|
| | C | H | N | |
| Calcd. | 64.18 | 10.44 | 9.36 | |
| Found | 64.17 | 10.48 | 9.33 | anhydrous |

B) [10-Octadecyl-1,4,7,10-tetraazacyclododecane-1,4,7-triacetato(3-)]gadolinium (CH$_3$COO)$_3$Gd (7.05 g; 17.3 mmol) was added to a suspension of the free ligand issued from the previous preparation (10.4 g; 17.3 mmol) in MeOH (400 mL) at 50° C. The reaction mixture was kept at 50° C. for 1 h, after which the clear solution was evaporated and dried under reduced pressure to give the title compound (11 g; 14.6 mmol). Yield 84%. HPLC: 100% (area %); K. F.: 1.83%; Weight loss (120° C.): 5.04%. The MS and IR spectra were consistent with the structure.

| | Elemental analysis (%): | | | |
|---|---|---|---|---|
| | C | H | N | Gd |
| Calcd. | 51.04 | 7.90 | 7.44 | 20.88 |
| Found | 50.84 | 7.96 | 7.19 | 20.39 |

EXAMPLE 3

[10-(2-Hydroxyoctadecyl)-1,4,7,10-tetraazacyclo-dodecane-1,4,7-triacetato-(3-)]gadolinium

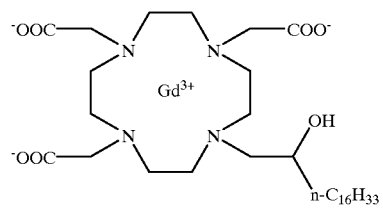

A) 10-(2-Hydroxyoctadecyl)-1,4,7,10-tetraazacyclododecane-1,4,7-triacetic acid

A solution of 1,2-epoxyoctadecane (17.4 g; 65 mmol) in abs. EtOH (100 mL) was added dropwise to a solution of 1,4,7,10-tetraazacyclododecane-1,4,7-triacetic acid tris-(1,1-dimethylethyl) ester (33.3 g; 65 mmol) in abs. EtOH and the mixture was heated to reflux. After 3 h, the reaction mixture was evaporated and the residue was dissolved in EtOAc and washed with brine. The organic phase was separated, dried over Na$_2$SO$_4$ and evaporated under reduced pressure. The residue was flash-chromatographed, (Eluent: CH$_2$Cl$_2$/MeOH=9/1 (v/v)).

The obtained product was dissolved in 5N HCl (500 mL) and the solution was heated to reflux. After 1.5 h, the mixture was evaporated and the residue purified by flash chromatography CH$_2$Cl$_2$/MeOH/NH$_4$OH 25% (w/w)=12/4/1 (v/v/v)).

The product was dissolved in H$_2$O and 6N HCl, the solution was loaded onto an Amberlite® XAD-8 resin column (800 mL) and eluted with a CH$_3$CN/H$_2$O gradient.

The fractions containing the product were evaporated and dried under reduced pressure to give the desired product (18 g; 29 mmol).

Yield 45%. Acidic titer (0.1 N NaOH): 95% HPLC: 94% (area %); K. F.: 7.10%. The $^{13}$C-NMR, MS and IR spectra were consistent with the structure.

| | Elemental analysis (%): | | | |
|---|---|---|---|---|
| | C | H | N | |
| Calcd. | 62.51 | 10.16 | 9.11 | |
| Found | 62.93 | 10.26 | 9.14 | anhydrous |

B) [10-(2-Hydroxyoctadecyl)-1,4,7,10-tetraazacyclododecane-1,4,7-triacetato-(3-)]gadolinium Gd$_2$O$_3$ (3.62 g.; 10 mmol) was added to a solution of the free ligand issued from the previous preparation (12.3 g; 20 mmol) in H$_2$O (150 mL) and the resulting suspension was heated at 50° C. for 40 h. The reaction mixture was filtered through a Millipore® apparatus (HA 0.45 μm filter); the filtrate (pH 6.7) was evaporated under reduced pressure and dried to give the title compound (14.2 g.; 18 mmol).

Yield 92%. Free ligand: 0.7%; HPLC: 95% (area %); K. F.: 7.94%.

The MS and IR spectra were consistent with the structure.

| | Elemental analysis (%): | | | |
|---|---|---|---|---|
| | C | H | N | Gd |
| Calcd. | 49.97 | 7.73 | 7.28 | 20.45 |
| Found | 49.98 | 7.88 | 7.29 | 20.57 | Anhydrous |

EXAMPLE 4

[10-[2-(Octadecylamino)-2-oxoethyl]-1,4,7,10-tetraazacyclo-dodecane-1,4,7-triacetato(3-)] gadolinium

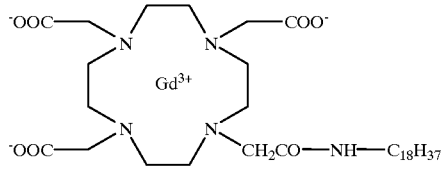

A) 2-Bromo-N-octadecylacetamide (C.A.S. registry number 15491-43-7)

A solution of bromoacetyl bromide (44.4 g; 0.22 mol) in CH$_2$Cl$_2$ (50 mL) was added dropwise in 2.5 h at 20° C. to a mixture of octadecylamine (59.3 g; 0.22 mol) and K$_2$CO$_3$ (30.4 g; 0.22 mol) in CH$_2$Cl$_2$ (600 mL) and H$_2$O (600 mL). After 16 h at room temperature the organic layer was separated, washed with H$_2$O, dried over Na$_2$SO$_4$ and evaporated. The crude product was purified by flash chromatography (CH$_2$Cl$_2$/MeOH=100/1 (v/v)) to give the desired product (60 g; 0.154 mol). Yield 70%. GC: 96% (area %), K. F.: <0.1%; $^1$H-NMR, $^{13}$C-NMR and MS spectra were consistent with the postulated structure.

Elemental analysis (%):

|  | C | H | N | Br | O |
|---|---|---|---|---|---|
| Calcd. | 61.52 | 10.33 | 3.59 | 20.46 | 4.09 |
| Found | 61.75 | 10.71 | 3.58 | 20.14 | 4.01 |

B) 10-[2-(Octadecylamino)-2-oxoethyl]-1,4,7,10-tetra-azacyclododecane-1,4,7-triacetic acid A mixture of 1,4,7,10-tetraazacyclododecane-1,4,7-triacetic acid tris(1,1-dimethylethyl) ester (24 g; 46.6 mmol) and 2-bromo-N-octadecylacetamide (18.2 g; 46.6 mmol) in EtOH (500 mL) was heated to reflux. After 2.5 h, the reaction mixture was evaporated, the residue was dissolved in $CH_2Cl_2$ and $CF_3COOH$ was added. After 15 min, the solvent was evaporated and the oily residue dissolved in $CF_3COOH$. After 16 h at room temperature the solution was evaporated and the oily residue was purified by flash chromatography ($CH_2Cl_2$/MeOH=3/1 (v/v); then $CH_2Cl_2$/MeOH/$NH_4OH$ 25% (w/w)=12/4/1 (v/v/v)).

The product was dissolved in $H_2O$ and 6N HCl, the solution was loaded onto an Amberlite® XAD-8 resin column and eluted with a $CH_3CN/H_2O$ gradient. The product elutes with 50% $CH_3CN$.

The fractions containing the product were evaporated and dried under reduced pressure to give the desired product (12 g; 18 mmol).

Yield 39%. Acidic titer (0.1 N NaOH): 91%; HPLC: 95% (area %); K. F.: 8.82%. The $^{13}$C-NMR, MS and IR spectra were consistent with the structure.

Elemental analysis (%):

|  | C | H | N |  |
|---|---|---|---|---|
| Calcd. | 62.26 | 9.99 | 10.68 |  |
| Found | 62.28 | 9.63 | 10.64 | anhydrous |

C) [10-[2-(Octadecylamino)-2-oxoethyl]-1,4,7,10-tetra-azacyclododecane-1,4,7-triacetato(3-)]gadolinium $Gd_2O_3$ (1.97 g; 5.4 mmol) was added to a solution of the free ligand from the previous preparation (7.12 g; 9.7 mmol) in $H_2O$ (310 mL) and the resulting suspension was heated to 50° C. for 9.5 h. The reaction mixture was filtered through a Millipore□ membrane (HA 0.45 μm filter) and the solution was evaporated to give the title compound (8.6 g; 9.5 mmol). Yield 98%. HPLC: 98% (area %); K. F.: 9.98%; MS and IR spectra were consistent with the structure.

Elemental analysis (%):

|  | C | H | N | Gd |  |
|---|---|---|---|---|---|
| Calcd. | 50.41 | 7.71 | 8.64 | 19.41 |  |
| Found | 50.52 | 7.78 | 8.65 | 19.32 | anhydrous |

EXAMPLE 5

[10-[2-(Dioctadecylamino)-2-oxoethyl]-1,4,7,10-tetraazacyclodo-decane-1,4,7-triacetato(3-)] gadolinium

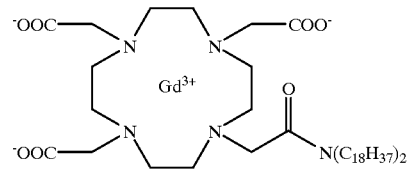

A) 2-Bromo-N,N-dioctadecylacetamide

This novel compound was prepared as follows: Bromoacetyl bromide (4.25 g; 21 mmol) was added dropwise to a solution of dioctadecylamine (10 g; 19 mmol) and $Et_3N$ (2.13 g; 21 mmol) in $CHCl_3$ (400 mL). After 4 h at room temperature the reaction solution was washed with $H_2O$, dried over $Na_2SO_4$ and evaporated. The residue was purified by flash chromatography (n-hexane/$Et_2O$=8/2 (v/v) to give the desired product (7.5 g; 11.5 mmol). Yield 61%. K. F.: <0.1%; The $^1$H-NMR, $^{13}$C-NMR, MS and IR spectra were consistent with the postulated structure Elemental analysis (%):

|  | C | H | N | Br |
|---|---|---|---|---|
| Calcd. | 70.99 | 11.91 | 2.18 | 12.43 |
| Found | 71.05 | 12.18 | 2.11 | 12.27 |

B) 10-[2-(Dioctadecylamino)-2-oxoethyl]-1,4,7,10-tetraazacyclo-dodecane-1,4,7-triacetic acid trihydrochloride A mixture of 1,4,7,10-tetraazacyclododecane-1,4,7-triacetic acid tris(1,1-dimethylethyl) ester (14.4 g; 28 mmol) and 2-bromo-N,N-dioctadecylamide (18.1 g; 28 mmol) in EtOH (800 mL) was heated to reflux. After 3 h the reaction mixture was evaporated and the residue was dissolved in $CH_2Cl_2$. The solution was washed with brine, dried over $Na_2SO_4$ and evaporated to give the crude alkylated ester. This product was suspended in 5N HCl and refluxed. After 2 h the suspension was filtered, the solid was washed with 5N HCl and dried under reduced pressure to give the desired compound (21.5 g; 21 mmol). Yield 95%. HPLC: 95.7% (area %). Argentometric titer (0.1 N $AgNO_3$): 98.5%; K. F.: 4.79%. The $^1$H-NMR, $^{13}$C-NMR, MS and IR spectra were consistent with the desired structure.

Elemental analysis (%):

|  | C | H | Cl | N |  |
|---|---|---|---|---|---|
| Calcd. | 61.37 | 10.29 | 10.45 | 6.88 |  |
| Found | 61.30 | 10.08 | 10.71 | 6.44 | Anydrous |

C) [10-[2-(Dioctadecylamino)-2-oxoethyl]-1,4,7,10-tetraaza-cyclododecane-1,4,7-triacetato(3-)]qadolinium A solution of $GdCl_3.6H_2O$ (5.8 g; 15.7 mmol) in $H_2O$ (50 mL) was added dropwise to a refluxing solution of the product from the previous preparation (16 g; 15.7 mmol) and 1 N NaOH (94.3 mL; 94.3 mmol) in abs. EtOH (1 L). After 1.5 h the mixture was cooled to room temperature, filtered and concentrated to half its volume, thus causing the precipitation of a solid which was filtered, washed with $H_2O$ and dried under reduced pressure. The solid was purified by flash chromatography (CH$_2$Cl$_2$/MeOH/Et$_3$N=16/4/1 (v/v/v)) and then suspended in H$_2$O at 50° C. for 3 h. The suspension was drained and the solid was washed with H$_2$O and dried under reduced pressure to give the title compound (11.5 g; 10.8 mmol). Yield 69%. HPLC: 96% (area %); K. F.: 3.93%. The MS and IR spectra were consistent with the structure.

| | Elemental analysis (%): | | | | |
|---|---|---|---|---|---|
| | C | H | N | Gd | |
| Calcd. | 58.78 | 9.30 | 6.59 | 14.80 | |
| Found | 58.59 | 9.14 | 6.36 | 14.26 | anhydrous |

EXAMPLE 6

[10-[2-Hydroxy-3-[(1-oxooctadecyl)oxy]propyl]-1,4,7,10-tetraaza-cyclododecane-1,4,7-triacetato(3-)] gadolinium

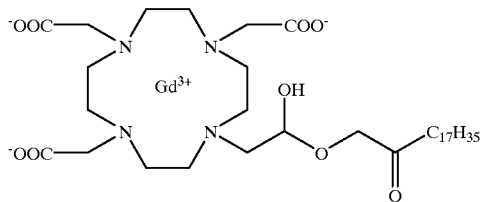

A) 10-(2,3-Dihydroxypropyl)-1,4,7,10-tetraazacyclododecane-1,4,7-triacetic acid tris(1,1-dimethylethyl) ester adduct with NaCl A solution of 2,3-epoxypropanol (3.7 g; 50 mmol) in abs. EtOH (80 mL) was added dropwise in 30 min to a refluxing solution of 1,4,7,10-tetraazacyclododecane-1,4,7-triacetic acid tris(1,1-dimethylethyl) ester (25.7 g; 50 mmol) in abs. EtOH (250 mL). After 2.5 h the solution was evaporated, the residue taken up with EtOAc and washed with brine. The organic phase was separated, dried (Na$_2$SO$_4$) and evaporated. The crude was purified by flash chromatography (CH$_2$Cl$_2$/MeOH=9/1 (v/v)) to give the desired compound (24 g; 37 mmol). Yield 74%. K. F.: 1.30%; The $^{13}$C-NMR, MS and IR spectra were consistent with the desired structure.

| | Elemental analysis (%): | | | | |
|---|---|---|---|---|---|
| | C | H | N | Cl | Na |
| Calcd. | 53.82 | 8.72 | 8.66 | 5.48 | 3.55 |
| Found | 53.95 | 8.87 | 8.72 | 5.47 | 3.48 anhydrous |

B) 10-[2-Hydroxy-3-[(1-oxooctadecyl)oxy]propyl]-1,4,7,10-tetra-azacyclododecane-1,4,7-triacetic acid tris-(1,1-dimethylethyl) ester adduct with NaCl A solution of dicyclohexylcarbodiimide (0.43 g; 2.1 mmol) in CHCl$_3$ (10 mL) was added dropwise in 10 min to a solution of stearic acid (0.44 g; 1.5 mmol) (commercial product), 10-(2,3-dihydroxypropyl)-1,4,7,10-tetraazacyclododecane-1,4,7-triacetic acid tris(1,1-dimethylethyl) ester adduct with NaCl (1 g; 1.5 mmol) and 4-(dimethylamino) pyridine (0.06 g; 0.5 mmol) (commercial product) in CHCl$_3$ (40 mL) at 0° C. The temperature of the reaction mixture was allowed to come back to normal. After 16 h, the mixture was concentrated to half its volume, the precipitate was filtered off and the solution evaporated. The crude was purified by flash chromatography (CH$_2$Cl$_2$/MeOH=10/1 (v/v)) to give the desired compound (0.95 g; 1.04 mmol). Yield 67%. The $^1$H-NMR, $^{13}$C-NMR, MS and IR spectra were consistent with the structure.

C) [10-[2-Hydroxy-3-[(1-oxooctadecyl)dxy]propyl]-1,4,7,10-tetra-azacyclo-dodecane-1,4,7-triacetato(3-)] gadolinium CF$_3$COOH (20 mL) was added to a solution of the product from the previous preparation (13.9 g; 15.2 mmol) in CH$_2$Cl$_2$ (5 mL). After 24 h the solution was evaporated and the residue taken up with more CF$_3$COOH (15 mL). After 6 h the mixture was evaporated and the crude desalted by dialysis (Spectra/Por® CE(Cellulose Ester) membrane MWCO 500) to afford a white solid (4 g). A portion of this solid (2.9 g) was dissolved in 2-propanol (100 mL) and H$_2$O (25 mL) at 80° C. then (CH$_3$COO)$_3$Gd (1.7 g) was added and the solution kept at 80° C. for 3 h. The reaction mixture was evaporated and the residue was purified by flash chromatography (CH$_2$Cl$_2$/MeOH/H$_2$O=5/5/1 (v/v/v)) to give the title compound (1.53 g; 1.8 mmol). Yield 12%.HPLC: 100% (area %); Weight loss (120° C.): 4.96%. The MS and IR spectra were consistent with the postulated structure.

| | Elemental analysis (%): | | | |
|---|---|---|---|---|
| | C | H | N | Gd |
| Calcd. | 49.98 | 7.55 | 6.66 | 18.69 |
| Found | 50.24 | 7.63 | 6.61 | 18.39 |

EXAMPLE 7

[10-[2-Hydroxy-3-[[[2-(Octadecyloxy)-1-[(octadecyloxy)methyl]-ethoxy]-acetyl]oxy]propyl]-1,4,7,10-tetraazacyclododecane-1,4,7-tri-acetato(3-)] gadolinium

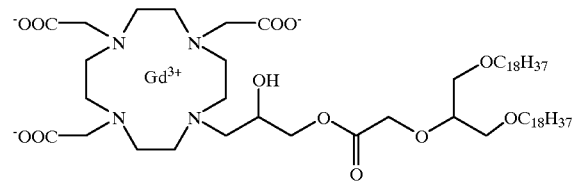

A) 1,3-Bis(octadecyloxy)-2-propanol (C.A.S. Registry No. 18794-74-6)

Epichlorohydrin (4.6 g; 50 mmol) was added in 5 min to excess stearyl alcohol (117 g;433 mmol) at 70° C. in the presence of 80% NaH mineral oil dispersion (1.65 g; 55 mmol) (commercial product). The mixture was stirred for 6 h, then cooled to room temperature and treated with Et$_2$O (2 L). The mixture was filtered and the solution evaporated. The crude product was crystallized four times from acetone to give the desired compound(16.5 g; 27.6 mmol). Yield 55%. K. F.: −0.1%. The $^1$H-NMR, $^{13}$C-NMR, MS and IR spectra were consistent with the above structure.

| Elemental analysis (%): | | |
|---|---|---|
| | C | H |
| Calcd. | 78.46 | 13.51 |
| Found | 78.63 | 13.61 |

B) [2-(Octadecyloxy)-1-[(octadecyloxy)methyl]ethoxy]-acetic acid (C.A.S. Registry No. 79979-56-9)

80% NaH mineral oil dispersion (2.65 g; 88 mmol) was added under nitrogen atmosphere to a solution of 1,3-bis(octadecyloxy)-2-propanol (6.92 g; 11.6 mmol) in THF (200 mL). The mixture was heated to reflux and a solution of $BrCH_2COOH$ (8.1 g; 58 mmol) in THF (50 mL) was added dropwise in 30 min. After another 30 min, MeOH was added, then the solvent was evaporated. The residue was dissolved in $Et_2O$, washed with 0.1 N HCl, dried and evaporated. The crude product was crystallized twice from EtOAc to give the desired compound (5.7 g; 8.7 mmol). Yield 75%. K. F.: 0.47%; the $^1$H-NMR, $^{13}$C-NMR, MS and IR spectra were consistent with the foregoing structure.

| Elemental analysis (%): | | | |
|---|---|---|---|
| | C | H | |
| Calcd. | 75.17 | 12.62 | |
| Found | 75.13 | 13.01 | anhydrous |

C) The title compound was then prepared, starting from [2-(octadecyloxy)-1-[(octadecyloxy)methyl]ethoxy]acetic acid and the intermediate (A) of Example 6, according to the synthetic method reported in Example 6

EXAMPLE 8

[6,9-Bis(carboxymethyl)-3-[2-(octadecylamino)-2-oxoet-hyl]-11-oxo-3,6,9,12-tetraazatriacontanoato(3-)]gadolinium

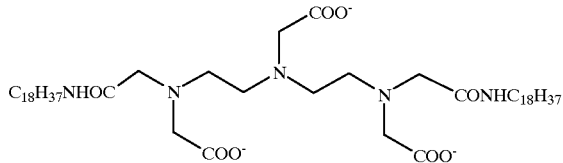

A) 6,9-Bis(carboxymethyl)-3-[2-(octadecylamino)-2-oxoethyl]-11-oxo-3,6,9,12-tetraazatriacontanoic acid (C.A.S. Registry Number 135546-68-8)

The product was synthesized following the procedure F. Jasanada and F. Nepveu in *Tetrahedron Lett.* 33 (1992), 5745–5748. K F: 0,54%. The $^1$H-NMR, $^{13}$C-NMR, MS and IR spectra were consistent with the foregoing structure.

| Elemental analysis (%): | | | | |
|---|---|---|---|---|
| | C | H | N | |
| Calcd. | 67.0 | 10.91 | 7.81 | |
| Found | 67.1 | 11.31 | 7.78 | anhydrous |

B) [6,9-Bis(carboxymethyl)-3-[2-(octadecylamino)-2-oxoethyl]-11-oxo-3,6,9,12-tetraazatriacontanoato(3-)]gadolinium This product was synthetized according to G. W. Kabalka et al. *Magn. Reson. Med.* 19 (1991), 406–415. Yield 82%. Weight loss (130° C.): 5.95%. The MS and IR spectra were consistent with the desired structure.

| Elemental analysis (%): | | | | |
|---|---|---|---|---|
| | C | H | N | Gd |
| Calcd. | 57.16 | 9.02 | 6.67 | 14.97 |
| Found | 57.09 | 9.37 | 6.57 | 14.85 |

EXAMPLE 9

6,9-Bis(carboxymethyl)-3-(2-oxo-6,9,12,15,18,21,24-hep-taoxa-3-azapentacosyl)-11-oxo-15,18,21,24,27,30,33-heptaoxa-3,6,9,12-tetraaza tetratriacontanoato(3-)]gadolinium

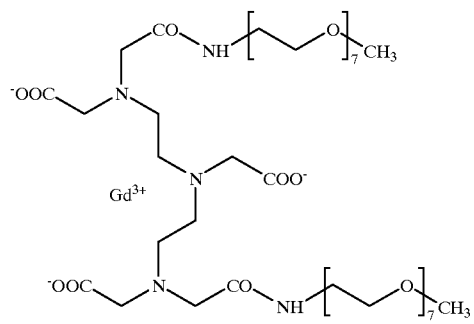

A) 6,9-Bis(carboxymethyl)-3-(2-oxo-6,9,12,15,18,21,24-heptaoxa-3-azapentacosyl)-11-oxo-15,18,21,24,27,30,33-heptaoxa-3,6,9,12-tetraaza tetratriacontanoic acid N,N-Bis[2-(2,6-dioxo-4-morpholinyl)ethyl]glycine (commercial product) (8.93 g; 25 mmol) was added to a solution of 2,5,8,11,14,17,20-heptaoxadocosan-22-amine (prepared according to WO 95/17380) (16.97 g; 50 mmol) in DMF (250 mL) at room temperature. After 2 h, the reaction mixture was evaporated and the residue was dissolved in $H_2O$ and 6N HCl. The solution (pH 2) was loaded onto an Amberlite$^\square$ XAD-1600 resin column and eluted with a $CH_3CN/H_2O$ gradient. The product starts eluting with 10% $CH_3CN$.

The fractions containing the product were evaporated and dried under reduced pressure to give the desired product (14 g; 13.5 mmol). Yield 54%. HPLC: 96% (area %). K. F.: 1.22%. The $^1$H-NMR, $^{13}$C-NMR, MS and IR spectra were consistent with the above structure.

| Elemental analysis (%): | | | | |
|---|---|---|---|---|
| | C | H | N | |
| Calcd. | 51.00 | 8.27 | 6.76 | |
| Found | 51.55 | 8.35 | 6.81 | anhydrous |

B) 6,9-Bis(carboxymethyl)-3-(2-oxo-6,9,12,15,18,21,24-heptaoxa-3-azapentacosyl)-11-oxo-15,18,21,24,27,30,33-hepta-oxa-3,6,9,12-tetraaza tetratriacontanoato(3-)]gadolinium Gd$_2$O$_3$ (1.86 g; 5.1 mmol) was added to a solution of the free ligand from the previous preparation (10.62 g; 10.2 mmol) in H$_2$O (200 mL) and the resulting suspension was heated at 50° C. for 7 h. The reaction mixture was filtered through a Millipore® apparatus (HA 0.45 µm filter); the filtrate was evaporated and dried under reduced pressure to give the title compound (11.9 g; 10 mmol). Yield 98%, Free ligand (0.001 M GdCl$_3$): 0.05% (w/w). HPLC: 98% (area %). K. F.: 1.69%. Weight loss (120° C.): 1.58%. The MS and IR spectra were consistent with the structure.

Elemental analysis (%):

|  | C | H | N | Gd |  |
| --- | --- | --- | --- | --- | --- |
| Calcd. | 44.40 | 6.94 | 5.88 | 13.21 |  |
| Found | 44.45 | 7.13 | 5.91 | 13.23 | anhydrous |

EXAMPLE 10

[6,9-Bis(carboxymethyl)-3-(2,16-dioxo-6,9,12-trioxa-3,15-diazatririacontanyl)-11,25-dioxo-15,18,21-trioxa-3,6,9,12,24-pentaazado-etraontanoato(3-)] gadolinium

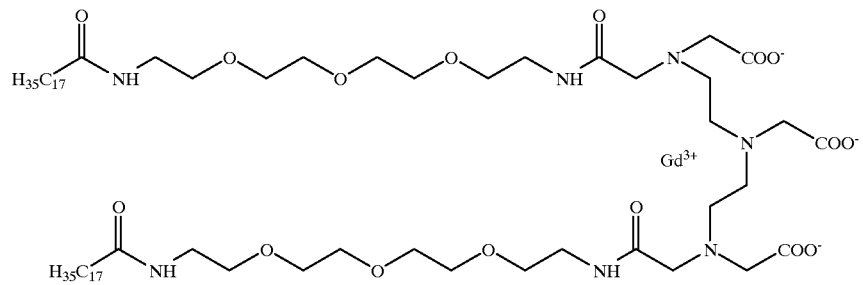

A) 1[(1-Oxooctadecyl)oxy]-2,5-pyrrolidinedione (C.A.S. Registry Number 14464-32-5)

This compound was synthetized according to M. Shin-itzky and R. Haimovitz in *J. Am. Chem. Soc.* 115 (1993), 12545–12549, and Y. Lapidot, S. Rappoport and Y. Wolman in *J. Lipid Res.* 8 (1967), 142–145. Yield: 86%. K.F.: <0.1%. The $^1$H-NMR, $^{13}$C-NMR and IR spectra were consistent with the structure.

Elemental analysis (%):

|  | C | H | N |  |
| --- | --- | --- | --- | --- |
| Calcd. | 69.25 | 10.30 | 3.67 |  |
| Found | 69.46 | 10.77 | 3.85 |  |

B) 3,6,9-Trioxaundecane-1,11-diamine (C.A.S. Registry No. 929-75-9)

This compound was prepared according to the method disclosed in Liebigs Ann. Chem. 2 (1990), 129–143.

Elemental analysis (%):

|  | C | N |
| --- | --- | --- |
| Calcd. | 49.98 | 14.57 |
| Found | 49.68 | 14.23 |

C) 13-Oxo-3,6,9-trioxa-12-azatriacontanylamine

H$_{35}$C$_{17}$-CONH—[(CH$_2$)$_2$-O]$_3$—(CH$_2$)$_2$—NH$_2$

1-[(1-Oxooctadecyl)oxy]-2,5-pyrrolidinedione (3.87 g; 10.1 mmol) in CHCl$_3$ (600 mL) was added dropwise in 6 h to a solution of 3,6,9-trioxaundecane-1,11-diamine (19.8 g; 103 mmol) in CHCl$_3$ (100 mL) at 20° C. The reaction mixture was evaporated, the residue treated with CH$_2$Cl$_2$ (50 mL) and the suspended solid filtered off. The solution was evaporated, the residue treated with H$_2$O and extracted with EtOAc. The organic phases were combined and dried. Concentration to small volume led to the precipitation of the desired compound (4.04 g; 8.8 mmol) which was collected by filtration. Yield 87%. The $^1$H-NMR, $^{13}$C-NMR, MS and IR spectra were consistent with the proposed structure.

Elemental analysis (%):

|  | C | H | N |  |
| --- | --- | --- | --- | --- |
| Calcd. | 68.08 | 11.87 | 6.11 |  |
| Found | 67.94 | 11.91 | 5.92 | anhydrous |

D) 6,9-Bis(carboxymethyl)-3-(2,16-dioxo-6,9,12-trioxa-3,15-diazatritriacontanyl)-11,25-dioxo-15,18,21-trioxa-3,6,9,12,24-pentaazadotetracontanoic acid N,N-Bis[2-(2,6-dioxo-4-morpholinyl)ethyl]glycine (commercial product) (6.45 g; 18 mmol) was added to a solution of 12-aza-13-oxo-3,6,9-trioxatriacontanylamine (16.57 g; 36 mmol) in DMF (300 mL) at 70° C. After 2 h the mixture was cooled to room temperature to give a precipitate that was filtered and washed with acetone. The crude was crystallized twice from acetone. The solid was filtered, washed with acetone and dried under reduced pressure to give the desired compound (17.35 g; 13.6 mmol). Yield 75%. HPLC: 98% (area %); K.F.: 0.99%. Weight loss (120° C.): 0.95%. The $^1$H-NMR, $^{13}$C-NMR, MS and IR spectra were consistent with the above structure.

| Elemental analysis (%): | | | |
|---|---|---|---|
| | C | H | N |
| Calcd. | 62.19 | 10.04 | 7.69 |
| Found | 62.36 | 10.00 | 7.55 | anhydrous |

E) [6,9-Bis(carboxymethyl)-3-(2,16-dioxo-6,9,12-trioxa3,15-diazatritriacontanyl)-11,25-dioxo-15,18,21-trioxa-3,6,9,12,24-pentaazadotetracontanoato(3-)]gadolinium $(CH_3COO)_3Gd.4H_2O$ (4.06 g; 10 mmol) was added to a solution of the product from the previous preparation (12.75 g; 10 mmol) in MeOH (600 mL) at 50° C. After 2 h the clear solution was evaporated and dried under reduced pressure to give the title compound (12.3 g; 8.6 mmol). Yield 86%. Free ligand (0.001 M $GdCl_3$): 0.02 (w/w). HPLC: 100% (area %); K.F.: 1.90%. Weight loss (120° C.): 3.02%. The MS and IR spectra were consistent with the structure.

| Elemental analysis (%): | | | | |
|---|---|---|---|---|
| | C | H | N | Gd |
| Calcd. | 55.47 | 8.75 | 6.86 | 11.00 |
| Found | 55.49 | 8.88 | 6.73 | 10.66 | anhydrous |

EXAMPLE 11

[6,9-Bis(carboxymethyl)-3-(2,14-dioxo-18,21,24,27,30,33,36-heptaoxa-3,15-diazaheptatriacontanyl)-11,23-dioxo-27,30,33,36,39,42,45-heptaoxa-3,6,9,12,24-pentaazahexatetracontanoato(3-)]gadolinium

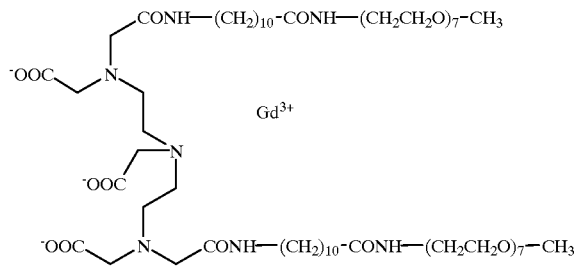

A) 11-[[(1,1-Dimethylethoxy)carbonyl]amino]undecanoic acid (C.A.S. Registry No. 10436-25-6)

11-Aminoundecanoic acid (3 g; 14.9 mmol) was suspended in a 10% solution of $Et_3N$ in MeOH (200 mL); dicarbonic acid bis(1,1-dimethylethyl) ester ($Boc_2O$) (3.58 g; 16.4 mmol) was added and the mixture was heated to 50° C. for 15 min. As soon as the aminoacid dissolved, reaction was complete. After evaporation of the solvent under reduced pressure, the triethylammonium salt of the product was treated with a 20% solution of citric acid in $H_2O$ and the free acid was extracted with EtOAc. The organic phase was separated, dried over $Na_2SO_4$ and then evaporated under reduced pressure to give the desired compound (4.45 g; 14.1 mmol). Yield 95%. HPLC: 97% (area %); K.F.: <0.1%. Weight loss (60 ° C.): 0.83%. The $^{13}$C-NMR, MS and IR spectra were consistent with the proposed structure.

| Elemental analysis (%): | | | |
|---|---|---|---|
| | C | H | N |
| Calcd. | 63.76 | 10.37 | 4.65 |
| Found | 63.73 | 10.38 | 4.63 |

B) 11-Amino-N-(3,6,9,12,15,18,21-heptaoxadocosyl)-undecanamide

To a stirred mixture of 11-[[(1,1-dimethylethoxy)carbonyl]amino]undecanoic acid (8.8 g; 29.2 mmol), 2,5,8,11,14,17,20-heptaoxadocosan-22-amine (prepared according to WO 95/17380) (10.9 g; 32.1 mmol) and diethyl cyanophosphonate (DEPC) (5.2 g; 32.1 mmol; 4.9 mL) in DMF (200 mL), maintained at 0° C., $Et_3N$ (3.3 g; 32.1 mmol; 4.5 mL) was added over 1 h. The reaction mixture was stirred at 0° C. for 30 min and then at room temperature for 1 h. The solvent was evaporated under reduced pressure, the crude was dissolved in 1.2 N HCl in MeOH and the resulting solution was stirred overnight.

(In an analogous preparation the above-mentioned crude was purified by washing the solution of the product in EtOAc with 5% aq. $NaHCO_3$ and identified as 11-[[(1,1-dimethylethoxy)carbonyl]amino]-N-(3,6,9,12,15,18,21-heptaoxadocosyl)undecanamide: HPLC: 91% (area %). Weight loss (120° C.): 0.71%; K.F.: 0.64%

| Elemental analysis (%): | | | |
|---|---|---|---|
| | C | H | N |
| Calcd. | 59.78 | 10.03 | 4.50 |
| Found | 59.59 | 10.48 | 4.51 | Anhydrous |

The $^{13}$C-NMR, MS and IR spectra were consistent with the structure).

After evaporation of the solvent under reduced pressure, the residue was dissolved in a saturated solution of $NaHCO_3$ and then washed with EtOAc. The aqueous phase was separated and acidified with 1N HCl until precipitation of the product occurred; the latter was filtered to give 11-amino-N-(3,6,9,12,15,18,21-heptaoxadocosyl)undecanamide salified with 1/3 HCl (11.9 g; 22.3 mmol). Yield 76%. HPLC: 95% (area %). K.F.: 0.30%. The $^{13}$C-NMR, MS and IR spectra were consistent with the foregoing structure.

| Elemental analysis (%): | | | | |
|---|---|---|---|---|
| | C | H | N | Cl |
| Calcd. | 58.38 | 10.24 | 5.24 | 2.09 |
| Found | 58.05 | 10.13 | 5.15 | 2.12 | anhydrous |

C) 6,9-Bis(carboxymethyl)-3-(2,14-dioxo-18,21,24,27,30,33,36-heptaoxa-3,15-diazaheptatriacontanyl)-11,23-dioxo-27,30,33,36,39,42,45-heptaoxa-3,6,9,12,24-pentaazahexatetracontanoic acid N,N-Bis[2-(2,6-dioxo-4-morpholinyl)ethyl]glycine (3.8 g; 10.6 mmol) (commercial product) was added to a suspension of 11-amino-N-(3,6,9,12,15,18,21-heptaoxadocosyl)undecan-amide (11.1 g; 21.1 mmol) in DMF (200 mL). After 15 min the reaction mixture became clear and the conversion was complete. The solvent was evaporated under reduced pressure, the residue was dissolved in $CHCl_3$ and washed with $H_2O$. The organic phase was separated, dried over $Na_2SO_4$ and then evaporated under reduced pressure. The solid was dissolved in $H_2O$ and loaded onto an Amberlite® XAD-7 HP resin column (700 mL) and eluted with a $CH_3CN/H_2O$ gradient. The fraction containing the product was evaporated to give the desired compound (11 g; 7.8 mmol). Yield 74%. HPLC: 85% (area %); K.F.: 0.49%. Weight loss (120 ° C.): 0.45%. The $^{13}C$-NMR, MS and IR spectra were consistent with the structure.

| Elemental analysis (%): | | | |
|---|---|---|---|
| | C | H | N |
| Calcd. | 56.51 | 9.13 | 6.99 |
| Found | 56.36 | 9.12 | 7.02 |

D) [6,9-Bis(carboxymethyl)-3-(2,14-dioxo-18,21,24,27,30, 33,36-heptaoxa-3,15-diazaheptatriacontanyl)-11,23-dioxo-27,30,33,36,39,42,45-heptaoxa-3,6,9,12,24-pentaazahexatetracontanoato(3-)]gadolinium $Gd_2O_3$ (0.9 g; 2.5 mmol) was added to a solution of the free ligand from the previous preparation (7 g; 5 mmol) in EtOH (100 mL) and $H_2O$ (150 mL), the resulting suspension was heated at 65° C. for 1 h. The reaction mixture was filtered through a Millipore® apparatus (HVLP type; 0.45 μm filter); the filtrate was evaporated under reduced pressure to give the title compound (7.5 g; 4.74 mmol). Yield 95%. Free gadolinium (0.001 M $Na_2EDTA$): <0.01% (w/w). HPLC: 96% (area %); K.F.: 1.69%. The MS and IR spectra were consistent with the structure.

| Elemental analysis (%): | | | | |
|---|---|---|---|---|
| | C | H | N | Gd |
| Calcd. | 50.91 | 8.03 | 6.30 | 10.10 |
| Found | 51.06 | 7.98 | 6.52 | 9.94 anhydrous |

EXAMPLE 12

[[6,9-Bis(carboxymethyl)-16-hydroxy-3-(7-hydroxy-2,7-dioxo-6,8-dioxa-3-aza-7-phosphatetracosanyl)-11,16-dioxo-15,17-dioxa-3,6,9,12-tetraaza-16-phosphatritriacontanoato(5-)]gadolinate(2-)] disodium salt

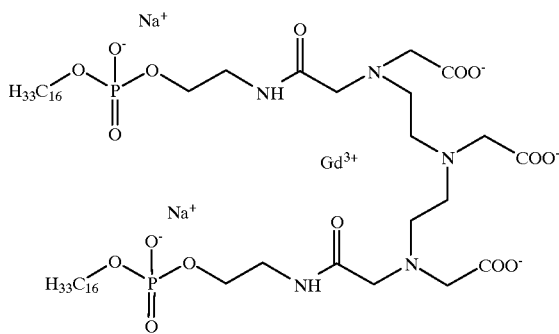

A) Phosphoric acid mono(2-aminoethyl) monohexadecyl ester [C.A.S. Registry Number 57303-02-3]

A solution of hexadecyl alcohol (26.2 g; 108 mmol) in THF (100 mL) was added dropwise in 30 min to a solution of $POCl_3$ (16.56 g; 108 mmol) and $Et_3N$ (12.35 g; 122 mmol) in THF (200 mL) at 0° C. After 5 min a solution of ethanolamine (7.2 g; 118 mmol) and $Et_3N$ (43.51 g; 430 mmol) in THF (60 mL) was added dropwise in 60 min. at 0° C. The reaction mixture was allowed to reach room temperature in 3 h; then it was heated at 40 ° C. and HCl 10% (100 mL) was added. After 2 h the mixture was cooled to room temperature and addition of $H_2O$ (200 mL) afforded a precipitate that was filtered, washed with $H_2O$ and dried under reduced pressure to give the desired product (33.4 g; 91 mmol). Yield 85%. K.F.: 0.53%. The $^1H$-NMR, $^{13}C$-NMR, MS and IR spectra were consistent with the structure.

| Elemental analysis (%): | | | | |
|---|---|---|---|---|
| | C | H | N | P |
| Calcd. | 59.15 | 11.03 | 3.83 | 8.47 |
| Found | 59.07 | 11.41 | 3.76 | 8.02 anhydrous |

B) 6,9-Bis(carboxymethyl)-16-hydroxy-3-(7-hydroxy-2,7-dioxo-6,8-dioxa-3-aza-7-phosphatetracosanyl)-11,16-dioxo-15,17-dioxa-3,6,9,12-tetraaza-16-phosphatritriacontanoic acid N,N-Bis[2-(2,6-dioxo-4-morpholinyl)ethyl]glycine (7.15 g; 20 mmol) (commercial product) was added to a suspension of phosphoric acid mono(2-aminoethyl) monohexadecyl ester (14.62 g; 40 mmol) in DMF (700 mL) at 75° C. to afford a solution after 15 min. After 5 h the reaction mixture was evaporated and the crude was treated with $H_2O$ and 2N HCl to give a solid that was filtered, washed with $H_2O$ and acetone. The solid was purified by flash chromatography ($CH_2Cl_2$/MeOH/$NH_4OH$ 25% (w/w)=6/3/1 (v/v/v)).

The fractions containing the product were combined and concentrated to 200 mL. Acidification with 2N HCl down to pH 1 led to the formation of a precipitate that was filtered, washed with $H_2O$ and acetone and dried under reduced pressure to give the desired compound (17 g; 15.6 mmol). Yield 78%. Acidic titer (0.1 N NaOH): 95%. HPLC: 99% (area %).

Weight loss (120° C.): 3.45%; K.F.: 3.06%. The $^1H$-NMR, $^{13}C$-NMR, MS and IR spectra were consistent with the structure.

| Elemental analysis (%): | | | | |
|---|---|---|---|---|
| | C | H | N | P |
| Calcd. | 55.18 | 9.17 | 6.43 | 5.69 |
| Found | 55.03 | 8.97 | 6.25 | 5.44 anhydrous |

C) [[6,9-Bis(carboxymethyl)-16-hydroxy-3-(7-hydroxy-2,7-dioxo-6,8-dioxa-3-aza-7-phosphatetracosanyl)-11,16-dioxo-15,17-dioxa-3,6,9,12-tetraaza-16-phosphatritriacontanoato(5-)]gadolinate(2-)]disodium salt $(CH_3COO)_3Gd \cdot 4H_2O$ (4.06 g; 10 mmol) was added to a solution of the free ligand from the previous preparation (10.88 g; 10 mmol) in MeOH (500 mL) and 1 N NaOH (20 mL; 20 mmol). After 24 h the clear solution was evaporated, the residue dissolved in $H_2O$ (200 mL) and the solution nanofiltered for 16 h.

The retentate was evaporated and dried under reduced pressure to give the title compound (11 g; 8.6 mmol). Yield 86%. HPLC: 99% (area %). Weight loss (120° C.): 4.33% K.F.: 4.23%. The MS and IR spectra were consistent with the structure.

| Elemental analysis (%): | | | | | | |
|---|---|---|---|---|---|---|
| | C | H | N | Gd | Na | P |
| Calcd. | 46.68 | 7.36 | 5.44 | 12.22 | 3.57 | 4.82 |
| Found | 46.50 | 7.66 | 5.44 | 11.99 | 3.48 | 4.47 | anhydrous |

EXAMPLE 13

[6,9-Bis(carboxymethyl)-11,19-dioxo-3-[2-[[(2-[2-[(1-oxooctadecyl)oxy]ethoxy]ethyl]amino]-2-oxoethyl]-15,18-dioxa-3,6,9,12-tetraazahexatriacontanoato(3-)]gadolinium

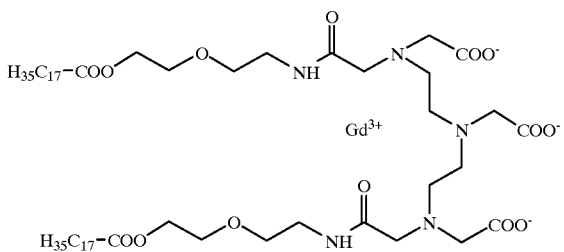

A) Octadecanoic acid 2-(2-aminoethoxy)ethyl ester hydrochloride 1.2 M HCl in $CH_3OH$ (30 mL) was added to a solution of 2-(2-aminoethoxy)ethanol (2.1 g; 20 mmol) (commercial product) in $CH_3OH$ (30 mL); after 30 min the solution was evaporated and dried under reduced pressure to give 2-(2-aminoethoxy)ethanol hydrochloride (2.9 g; 20 mmol).

Stearoyl chloride (6.4 g; 21 mmol) (commercial product) was added dropwise in 5 min to a solution of 2-(2-aminoethoxy)ethanol hydrochloride (2.9 g; 20 mmol) in DMF (50 mL) at room temperature to afford a suspension. After 16 h, the suspension was diluted with acetone and the precipitated solid filtered and washed with acetone. The crude was crystallized from EtOAc; the solid was filtered, washed with EtOAc and dried under reduced pressure to give the desired compound (3.3 g; 8 mmol). Yield 40%. Acidic titer (0.1 N NaOH): 93%. K.F.: 1.06%. The $^1$H-NMR, $^{13}$C-NMR, MS and IR spectra were consistent with the structure.

| Elemental analysis (%): | | | | |
|---|---|---|---|---|
| | C | H | N | Cl |
| Calcd. | 64.75 | 11.36 | 3.43 | 8.69 |
| Found | 64.82 | 11.41 | 3.52 | 8.90 | anhydrous |

B) 6,9-Bis(carboxymethyl)-11,19-dioxo-3-[2-[[2-[2-[(1-oxooctadecyl)oxy]ethoxy]ethyl]amino]-2-oxoethyl]-15,18-dioxa-3,6,9,12-tetraazahexatriacontanoic acid N,N-Bis(2-(2,6-dioxo-4-morpholinyl)ethyl]glycine (1.9 g; 5.5 mmol) (commercial product) was added to a solution of octadecanoic acid 2-(2-aminoethoxy)ethyl ester hydrochloride (4.5 g; 11 mmol) and $Et_3N$ (1.5 g; 14 mmol) in DMF (150 mL) at 60° C. After 5 min the temperature was decreased to 45° C. After 2.5 h the mixture was cooled to room temperature to give a precipitate that was filtered, washed with acetone/$H_2O$ 15/5, then with acetone. The crude was dissolved in acetone and 0.1 N HCl and the solution heated at 50° C. After 10 min the solution was cooled to room temperature to afford a precipitate which was filtered, washed with acetone/$H_2O$ 15/5 then with acetone and dried under reduced pressure to give the desired compound (1.7 g; 1.5 mmol). Yield 27%. HPLC: 100% (area %). HPCE: 100% (area). K.F.: 3.11%. Weight loss (120 ° C.): 4.49%. The $^1$H-NMR, $^{13}$C-NMR, MS and IR spectra were consistent with the structure.

| Elemental analysis (%): | | | |
|---|---|---|---|
| | C | H | N |
| Calcd. | 63.30 | 9.98 | 6.36 |
| Found | 63.29 | 9.95 | 6.50 |

C) [6,9-Bis(carboxymethyl)-11,19-dioxo-3-[2-[[2-[2-[(1-oxooctadecyl)oxy]ethoxy]ethyl]amino]-2-oxoethyl]-15,18-dioxa-3,6,9,12-tetraazahexatriacontanoato(3-)]gadolinium $(CH_3COO)_3Gd.4H_2O$ (1.11 g; 2.7 mmol) was added to a solution of the free ligand from the previous preparation (3 g; 2.7 mmol) in MeOH (150 mL) at 40° C. After 1 h the clear solution was evaporated and dried under reduced pressure. The crude was purified by flash chromatography ($CH_3OH$) to give the title compound (3.2 g; 2.5 mmol). Yield 94%. HPCE: 100% (area %). K.F.: 4.07%. Weight loss (120° C.): 4.08%. the MS and IR spectra were consistent with the structure.

| Elemental analysis (%): | | | | |
|---|---|---|---|---|
| | C | H | N | Gd |
| Calcd. | 55.52 | 8.52 | 5.58 | 12.53 |
| Found | 55.50 | 8.52 | 5.58 | 12.62 | anhydrous |

EXAMPLE 14

[[N,N'-[[[2-(Octadecylamino)-2-oxoethyl]imino]di-2,1-ethanediyl]bis[N-(carboxymethyl)glycinato(4-)]] gadolinate(1-)]sodium salt

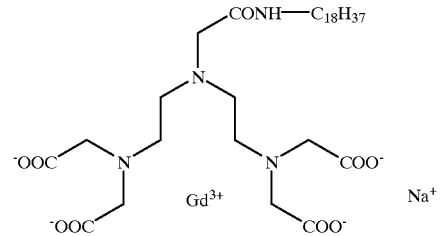

A) N,N-bis[2-[bis[2-(1,1-dimethylethoxy)-2-oxoethyl] amino]-ethyl]glycine

The compound was prepared according to the method disclosed in patent application WO-A-95/32741.

B) N,N'-[[[2-(Octadecylamino)-2-oxoethyl]imino]di-2,1-ethanediyl]bis[N-[2-(1,1-dimethylethoxy)-2-oxoethyl]glycine 1,1-dimethylethyl ester]

Isobutyl chloroformate (205 mg; 1.65 mmol; 215 μL) was added dropwise to a solution of the product from the previous preparation (950 mg; 1.54 mmol) and Et$_3$N (165 mg; 1.65 mmol; 230 1L) in THF (50 mL) at −5° C. and under nitrogen. After 15 min a suspension of octadecylamine (450 mg; 1.65 mmol) in THF (50 mL) was added to the reaction mixture at −5° C. After 20 min the reaction mixture was allowed to rise to room temperature and stirred overnight. The suspension was filtered to remove the residual octadecylamine and the solution was evaporated under reduced pressure. The residue was dissolved in Et$_2$O and the solution washed with 5% aq. NaHCO$_3$. The organic phase was dried over Na$_2$SO$_4$ and then evaporated under reduced pressure. The crude product was purified by flash chromatography (CH$_2$Cl$_2$/MeOH=100/2 (v/v)) to give the desired compound (1.1 g; 1.26 mmol). Yield 80%. HPLC: 94% (area %). The $^{13}$C-NMR, MS and IR spectra were consistent with the structure.

C) N,N'-[[[2-(Octadecylamino)-2-oxoethyl]imino]di-2,1-ethanediyl]bis[N-(carboxymethyl)glycine]

0.5 M H$_2$SO$_4$ (100 mL; 50 mmol) was added dropwise to a solution of the tetraester from the previous preparation (21 g; 24.3 mmol) in dioxane (150 mL) and the resulting mixture was heated at 90° C. for 4 h. The pH of the solution was adjusted to 5 with 2 N NaOH (10 mL) and the solvent was evaporated under reduced pressure. The residue was dissolved in CHCl$_3$/MeOH (4:1) and the resulting suspension was filtered and evaporated under reduced pressure. The crude product was purified by flash chromatography (CH$_2$Cl$_2$/MeOH/NH$_4$OH 25% (w/w)=6/3/1 (v/v/v)). The product was dissolved in H$_2$O (150 mL) and 12 N HCl (7 mL) and desalted by elution through an Amberlite▢ XAD 7-HP resin column with a CH$_3$CN/H$_2$O gradient. The fractions containing the product were evaporated to give the desired compound (4 g; 6.2 mmol). Yield 25%. HPLC 99% (area %). K.F.: 3.77%. The $^{13}$C-NMR, MS and IR spectra were consistent with the structure.

| Elemental analysis (%): | | | | |
|---|---|---|---|---|
| | C | H | N | |
| Calcd. | 59.60 | 9.38 | 8.69 | |
| Found | 58.70 | 9.21 | 8.51 | anhydrous |

D) [[N,N'-[[[2-(Octadecylamino)-2-oxoethyl]imino]di-2,1-ethanediyl]bis[N-(carboxymethyl)glycinato(4-)]] gadolinate(1-)]sodium salt 1 N NaOH (4.5 mL) was added to a suspension of the free ligand from the previous preparation (2.9 g; 4.5 mmol) in 1:1 H$_2$O/CH$_3$CN (600 mL). A solution of GdCl$_3$.6H$_2$O (1.66 g; 4.48 mmol) in H$_2$O (50 mL) was added dropwise to the reaction mixture maintained at pH 6.8 by the addition of 1 N NaOH (13.5 mL). After 2 h the solution was evaporated; the residue was dissolved in H$_2$O and desalted by elution through an Amberlite® XAD 7-HP resin column (250 mL) with a H$_2$O/CH$_3$CN gradient.

The fractions containing the product were evaporated. The solid residue was dissolved in H$_2$O and the solution eluted through a Dowex® CCR 3LB weak cation exchange resin column (Na$^+$ form, 20 mL). The eluate was evaporated and dried under reduced pressure to give the title compound (1.35 g; 1.64 mmol). Yield 35%. HPLC: 100% (area %). K.F.: 8.85%. Weight loss (120° C.): 8.15%. The MS and IR spectra were consistent with the structure.

| Elemental analysis (%): | | | | | |
|---|---|---|---|---|---|
| | C | H | N | Gd | Na |
| Calcd. | 46.81 | 6.87 | 6.82 | 19.15 | 2.80 |
| Found | 46.79 | 7.03 | 6.74 | 18.96 | 2.68 |

EXAMPLE 15

[N$^2$,N$^2$-Bis[2-[bis(carboxymethyl)amino]ethyl]-N$^6$-(1-oxooctadecyl)-L-lysinato(5-)]gadolinate(2-)] disodium salt

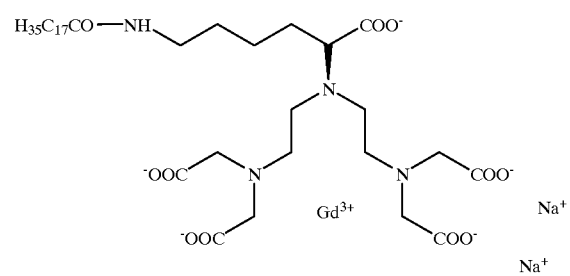

A) N$^2$,N$^2$-Bis[2-[bis[2-(1,1-dimethylethoxy)-2-oxoethyl]-amino]-ethyl]-L-lysine 1,1-dimethylethyl ester This product was prepared according to Example 2 of WO 98/05626. The $^{13}$C-NMR, $^1$H-NMR, MS and IR spectra were consistent with the disclosed structure.

| Elemental analysis (%): | | | |
|---|---|---|---|
| | C | H | N |
| Calcd. | 61.26 | 9.74 | 7.52 |
| Found | 61.43 | 10.25 | 7.48 |

B) N$^2$,N$^2$-Bis[2-[bis(2-(1,1-dimethylethoxy)-2-oxoethyl]amino]-ethyl]-N$^6$-(1-oxooctadecyl)-L-lysine-(1,1-dimethylethyl)-ester Stearoyl chloride (5.45 g; 18 mmol) dissolved in CHCl$_3$ (60 mL) was added dropwise in 1 h to a solution of N$^2$,N$^2$-bis[2-[bis[2-(1,1-dimethylethoxy)-2-oxoethyl]amino]ethyl]-L-lysine 1,1-dimethylethyl ester (13.5 g; 18 mmol) in CHCl$_3$ (300 mL) at 0° C. After 10 min the reaction mixture was allowed to rise to room temperature and TLC analysis showed the complete conversion of the starting materials. The solution was washed with 5% aq. NaHCO$_3$, the organic phase was separated, dried over Na$_2$SO$_4$ and then evaporated under reduced pressure. The crude product was purified by flash chromatography (n-hexane/EtOAc=6/4 (v/v)) to give the desired product (11.3 g; 11.2 mmol). Yield 62%. HPLC: 95% (area %). The $^{13}$C-NMR, MS and IR spectra were consistent with the structure.

C) N$^2$,N$^2$-Bis[2-[bis(carboxymethyl)amino]ethyl]-N$^6$-(1-oxooctadecyl)-L-lysine N$^2$,N$^2$-Bis[2-[bis(2-(1,1-dimethylethoxy)-2-oxoethyl]-amino]ethyl]-N$^6$-(1-oxooctadecyl)-L-lysine 1,1-dimethylethyl ester (9 g, 8.9 mmol) was dissolved in 6 N HCl (200 mL) and the solution was stirred for 3 days. The reaction mixture was directly loaded onto an Amberlite▢ XAD 7-HP resin column and desalted by elution with a CH$_3$CN/H$_2$O gradient.

The solid obtained from the column was completely converted into the expected acid by treatment with neat CF$_3$COOH for 2 h. CF$_3$COOH was eliminated by repeated dilution with CH$_2$Cl$_2$ and Et$_2$O followed each time by evaporation under reduced pressure. The residue was dried to give the desired product (3.1 g; 4.06,mmol). Yield 45%. HPLC: 94.4% (area %). Weight loss (120° C.): 4.22%. The $^{13}$C-NMR, MS and IR spectra were consistent with the structure.

| | Elemental analysis (%): | | |
|---|---|---|---|
| | C | H | N |
| Calcd. | 59.16 | 9.10 | 7.67 |
| Found | 59.02 | 9.38 | 7.63 |

D) [N$^2$,N$^2$-Bis[2-[bis(carboxymethyl)amino]ethyl]-N$^6$-(1-oxooctadecyl)-L-lysinato(5-)]gadolinate(2-)]disodium salt The free ligand from the previous preparation (2.16 g; 2.96 mmol) was suspended in H$_2$O (50 mL) and dissolved by addition of 1 N NaOH (5.9 mL). Dropwise addition of a 1 M aq. solution of (CH$_3$COO)$_3$Gd (2.96 mL) led to the precipitation of a solid, which was dissolved by addition of EtOH (150 mL). The solvent was evaporated under reduced pressure to give the title compound (2.57 g; 2.66 mmol). Yield 90%. HPLC: 99% (area %). K.F.: 3.81%. Weight loss (120° C.) 3.84%. The MS and IR spectra were consistent with the structure.

| | Elemental analysis (%): | | | | |
|---|---|---|---|---|---|
| | C | H | N | Gd | Na |
| Calcd. | 46.54 | 6.62 | 6.03 | 16.92 | 4.95 |
| Found | 46.17 | 6.38 | 5.67 | 16.93 | 5.42 |

EXAMPLE 16

[[N$^2$, N$^2$-Bis[2-[bis(carboxymethyl)amino]ethyl]-N$^6$-[[[3β)-cholest-5-en-3-yl]oxy]carbonyl]-L-lysinato(5-)]gadolinate(2-)]disodium salt

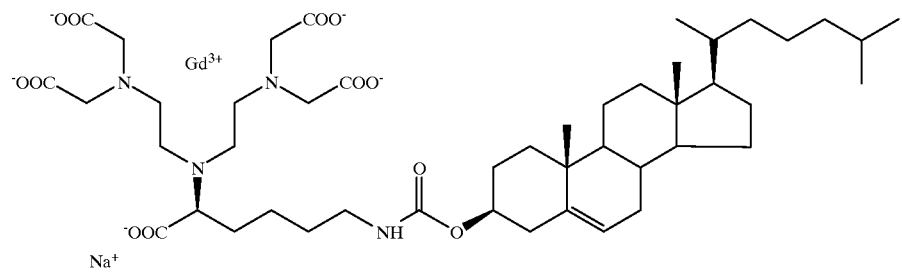

A) N$^2$,N$^2$-Bis[2-[bis[2-(1,1-dimethylethoxy)-2-oxoethyl)-amino]-ethyl]-N$^6$-[[[(3β)-cholest-5-en-3-yl]oxy]carbonyl]-L-lysine 1,1-di-methylethyl ester A solution of cholesteryl chloroformate (11 g; 22 mmol) (commercial product) in CHCl$_3$ (60 mL) was added in 1 h to a solution of N$^2$,N$^2$-bis[2-[bis[2-(1,1-dimethylethoxy)-2-oxoethyl]amino]ethyl]-L-lysine 1,1-dimethyl ethyl ester (14.9 g; 20 mmol) (prepared according to Example 2 of WO 98/05626) in CHCl$_3$ (150 mL). The reaction mixture was stirred overnight. The solution was then washed with 5% aq. NaHCO$_3$, the organic phase was separated, dried over Na$_2$SO$_4$ and then evaporated under reduced pressure. The crude product was purified by flash chromatography (n-Hexane/EtOAc=85/15 (v/v)) to give the desired compound (18.2 g; 15.7 mmol). Yield 78%. HPLC: 94% (area %). Weight loss (100 ° C.): 1.23%. The $^{13}$C-NMR, MS and IR spectra were consistent with the structure.

| | Elemental analysis (%): | | |
|---|---|---|---|
| | C | H | N |
| Calcd. | 68.48 | 10.10 | 4.84 |
| Found | 68.89 | 10.08 | 4.75 |

B) N$^2$,N$^2$-Bis[2-[bis(carboxymethyl)amino]ethyl]-N$^6$-[[[(3β)-cholest-5-en-3-yl]oxy]carbonyl]-L-lysine 12.6 g of the product from the previous preparation (10.88 mmol) were dissolved in formic acid (250 mL) and refluxed for 1.5 h. The solution was evaporated under reduced pressure, the crude was suspended in water, stirred for 30 min and filtered to give the desired compound (7.8 g; 8.5 mmol). Yield 79%. HPLC: >91% (area %). K.F.: 3.73%. The $^{13}$C-NMR, MS and IR spectra were consistent with this structure.

| | Elemental analysis (%): | | | |
|---|---|---|---|---|
| | C | H | N | |
| Calcd. | 62.99 | 8.73 | 6.39 | |
| Found | 62.70 | 8.89 | 6.31 | anhydrous |

C) [[N$^2$,N$^2$-Bis[2-[bis(carboxymethyl)amino]ethyl]-N$^6$-[[[(3β)-cholest-5-en-3-yl]oxy]carbonyl]-L-lysinato(5-)] gadolinate(2-)]disodium salt 5.3 g of the free ligand from the previous preparation (5.8 mmol) were suspended in H$_2$O (300 mL) and dissolved by the addition of 2 N NaOH (5.8 mL). A solution of GdCl$_3$.6H$_2$O (2.16 g; 5.8 mmol) in H$_2$O (10 mL) was added dropwise to the reaction mixture maintained at pH 6.8 by the addition of 2 N NaOH (8.7 mL). After 1 h the solution was concentrated to 50 mL, the addition of CH$_3$CN led to the precipitation of the title compound, which was filtered and dried (4.94 g; 4.60 mmol). Yield 79%. HPLC: >89% (area %). K.F.: 10.12%. Weight loss (120° C.): 11.89%. The MS and IR spectra were consistent with the structure.

| Elemental analysis (%): | | | | | |
|---|---|---|---|---|---|
| | C | H | N | Gd | Na |
| Calcd. | 51.38 | 6.66 | 5.21 | 14.62 | 4.28 |
| Found | 51.47 | 6.83 | 5.17 | 14.51 | 4.02 |

EXAMPLE 17

[10-[[2-[2-[2-(Dioctadecylamino)-2-oxoethoxy]-2-oxoethyl]amino]

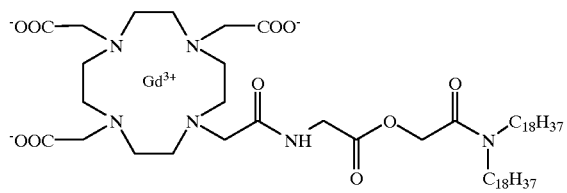

2-oxoethyl]-1,4,7,10-tetraazacyclododecane-1,4,7-triacetato(3-)]gadolinium

A) N-Octadecyl-1-octadecanamine(dioctadecylamine) (C.A.S. Registry No. 112-99-2.

A1) Dioctadecylcyanamide (C.A.S. Registry No. 113576-09-3)

Cyanamide (5 g; 119 mmol) was added to stirred 50% aq. NaOH (100 g). The mixture was cooled to 25° C., then a solution of Aliquat□ 336 (trioctylmethylammonium chloride) (2.42 g; 6 mmol) (commercial product) and 1-bromooctadecane (40.37 g; 121 mmol) in toluene (50 mL) was added. The mixture was vigorously stirred at 55° C. for 6 h. The organic phase was separated and evaporated to give the desired compound (38 g). The crude product was used in the hydrolysis step without any further purification. K.F.: <0.1%. The $^1$H-NMR, $^{13}$C-NMR, MS and IR spectra were consistent with the structure.

| Elemental analysis (%): | | | |
|---|---|---|---|
| | C | H | N |
| Calcd. | 81.24 | 13.64 | 5.12 |
| Found | 80.86 | 13.91 | 5.19 |

A2) N-Octadepyl-1-octadecanamine(dioctadecylamine)

The crude dioctadecylcyanamide (38 g) was suspended in 2.75 M $H_2SO_4$ (150 mL) and the mixture was refluxed for 2.5 h. After cooling to room temperature $H_2O$ (100 mL), 30% NaOH (100 mL) and CHCl$_3$ (300 mL) were added. The organic phase was separated, dried and evaporated. The solid residue was suspended in Et$_2$O and stirred for 1 h. The solid was filtered and washed with to give the desired compound (15.3 g; 29.3 mmol). Yield 48%. K.F.: 0.20%. The $^1$H-NMR, $^{13}$C-NMR, MS and IR spectra were consistent with the structure.

| Elemental analysis (%): | | | |
|---|---|---|---|
| | C | H | N |
| Calcd. | 82.83 | 14.48 | 2.68 | |
| Found | 82.61 | 14.65 | 2.69 | anhydrous |

B) 2-Hydroxy-N,N-dioctadecylacetamide (Acetyloxy)acetyl chloride (3.8 g; 28.1 mmol) (commercial product) dissolved in CHCl$_3$ (150 mL) was added dropwise to a solution of dioctadecylamine (13.3 g; 25.5 mmol) and Et$_3$N (3.9 mL; 28.1 mmol) in CHCl$_3$ (350 mL) and the solution was stirred at room temperature overnight. MeOH (250 mL) and 2 N NaOH (50 mL) were added to the solution. $H_2O$ was added to the reaction mixture and a two phase system was obtained. The lower organic layer was separated and evaporated. The solid residue was suspended in n-hexane and filtered to give the desired compound (12.1 g;20.9 mmol). Yield 82%. HPLC: 96% (area %). K.F.: <0.1%. The $^{13}$C-NMR, MS and IR spectra were consistent with the structure.

| Elemental analysis (%): | | | |
|---|---|---|---|
| | C | H | N |
| Calcd. | 78.69 | 13.38 | 2.41 |
| Found | 78.56 | 13.44 | 2.44 |

C) N-[(Phenylmethoxy)carbonyl]glycine[2-(dioctadecylamino)-2-oxoethyl) ester

A solution of DCC (2.1 g; 10.3 mmol) in CHCl$_3$ (50 mL) was added dropwise to a solution of 2-hydroxy-N,N-dioctadecylacetamide (5 g; 8.6 mmol) and Z-glycine (2 g; 9.5 mmol) in CHCl$_3$ (250 mL). DMAP (0.1 g; 0.9 mmol) was added to the resulting solution. After 1 h the reaction mixture was filtered and the solvent was evaporated. The crude was purified by flash chromatography (n-Hexane/EtOAc=7/3 (v/v)) to give the desired compound (5.6 g; 7.3 mmol). Yield 84%. HPLC: 99% (area %). K.F.: <0.1%. The $^{13}$C-NMR, MS and IR spectra were consistent with the structure.

| Elemental analysis (%): | | | |
|---|---|---|---|
| | C | H | N |
| Calcd. | 74.76 | 11.24 | 3.63 |
| Found | 75.45 | 11.47 | 3.68 |

D) Glycine [2-(dioctadecylamino)-2-oxoethyl) ester hydrochloride

10% Pd/C (150 mg) was added to a solution of N-((phenylmethoxy)-carbonyl]glycine[2-(dioctadecylamino)-2-oxoethyl] ester (1.2 g; 1.4 mmol) in EtOAc (100 mL) and the suspension was stirred for 3 h under hydrogen atmosphere at room temperature. After filtration (through a Millipore® filter FT 0.45 μm) 1.2 M HCl in MeOH (1.3 mL; 1.6 mmol) was added dropwise to the resulting solution obtaining the precipitation of a white solid that was filtered to give the desired compound (830 mg; 1.2 mmol). Yield 86%. HPLC: 100% (area %). K.F.: 0.22%. The MS and IR spectra were consistent with the structure.

| Elemental analysis (%): | | | | |
|---|---|---|---|---|
| | C | H | N | Cl |
| Calcd. | 71.33 | 12.48 | 4.16 | 5.26 |
| Found | 71.72 | 12.48 | 4.30 | 5.30 | anhydrous |

E) 1,4,7,10-tetraazacyclododecane-1,4,7,10-tetraacetic acid tris(phenylmethyl) ester E1) 1,4,7,10-Tetraazacyclododecane-1-acetic acid (1,1-dimethylethyl) ester A solution of t-butyl bromoacetate (25.3 g; 130 mmol) in $CHCl_3$ (500 mL) (commercial product) was added dropwise in 7 h to a solution of 1,4,7,10-tetraazacyclododecane (112.3 g; 650 mmol) (commercial product) in $CHCl_3$ (2 L) maintained under nitrogen at room temperature. After 14 h the solution was concentrated to 800 mL, washed with $H_2O$, dried and evaporated to give the desired compound (39 g; 129 mmol). Yield 99%. GC: 92% (area %). K.F.: 0.42%. The $^{13}$C-NMR, MS and IR spectra were consistent with the structure.

| Elemental analysis (%): | | | | | |
|---|---|---|---|---|---|
| | C | H | N | Na | Cl |
| Calcd. | 56.20 | 10.06 | 18.56 | = | = |
| Found | 56.36 | 10.34 | 18.84 | <0.1 | 4.56 | anhydrous |

E2) 1,4,7,10-Tetraazacyclododecane-1,4,7-tetraacetic acid (1,1-dimethyl-ethyl) tris(phenylmethyl) ester A solution of 1,4,7,10-tetraazacyclododecane-1-acetic acid (1,1-dimethylethyl) ester (36 g; 126 mmol) in DMF (200 mL) was added dropwise in 7 h to a suspension of benzyl bromoacetate (94.96 g; 414 mmol) and $K_2CO_3$ (86.8 g; 628 mmol) in DMF (250 mL) maintained under nitrogen at room temperature. After 14 h the suspension was filtered and the solution evaporated to dryness. The residue was dissolved in EtOAc, washed with $H_2O$, then with brine. The organic phase was separated, dried over $Na_2SO_4$ and evaporated. The residue was purified by flash chromatography ($CH_2Cl_2$/MeOH=15/1 (v/v)) to give the desired compound (51 g; 65 mmol). Yield 51%. HPLC: 90% (area %). K.F.: 0.48%. The $^{13}$C-NMR, MS and IR spectra were consistent with the structure.

| Elemental analysis (%): | | | | | |
|---|---|---|---|---|---|
| | C | H | N | Na | Cl |
| Calcd. | 62.38 | 6.91 | 7.10 | 2.91 | 4.49 |
| Found | 61.77 | 6.74 | 6.90 | 2.90 | 4.95 | anhydrous |

E3) 1,4,7,10-Tetraazacyclododecane-1,4,7-tetraacetic acid tris(phenyl-methyl) ester 1,4,7,10-Tetraazacyclododecane-1,4,7,10-tetraacetic acid (1,1-dimethyl-ethyl) tris(phenylmethyl) ester adduct with NaCl (47.11 g; 60 mmol) was dissolved in dioxane (500 mL). The solution was treated with 12 N HCl (500 mL) under nitrogen at room temperature, obtaining a precipitate. After 16 h the suspension was evaporated and the residue dissolved in $H_2O$ by ultrasound sonication. The solution (pH 2) was loaded onto an Amberlite® XAD-1600 resin column (900 mL) and eluted with a $CH_3CN/H_2O$ gradient. The fractions containing the product were concentrated to remove $CH_3CN$, then extracted with EtOAc. The organic phase was dried over $Na_2SO_4$ and evaporated. The residue was triturated with EtOAc to give the desired compound (21 g; 31 mmol). Yield 52%. HPLC: 99% (area %). K.F.: <0.1%. The $^{13}$C-NMR, MS and IR spectra were consistent with the structure.

| Elemental analysis (%): | | | |
|---|---|---|---|
| | C | H | N |
| Calcd. | 65.86 | 6.87 | 8.30 |
| Found | 66.00 | 7.03 | 8.33 |

F) 10-[[2-(2-(2-(Dioctadecylamino)-2-oxoethoxy]-2-oxoethyl]-amino]-2-oxoethyl]-1,4,7,10-tetraazacyclododecane-1,4,7-triacetic acid tris(phenylmethyl) ester To a suspension of 1,4,7,10-tetraazacyclododecane-1,4,7-tetraacetic acid tris(phenylmethyl) ester (2.7 g; 4 mmol) and glycine [2-(dioctadecylamino)-2-oxoethyl]ester hydrochloride (3 g; 4.4 mmol) in $CHCl_3$ (250 mL) was added DIEA (diisopropylethylamine) (1.5 mL; 8.8 mmol). BOP ((benzotriazol-1-yloxy)tris(dimethylamino)phosphonium hexafluorophosphate, commercial product) (2.2 g; 4.8 mmol) was added to the resulting solution, which was stirred at room temperature for 2 h. The solvent was evaporated and the solid residue was suspended in 9:1 i-PrOH/$H_2O$ and filtered to obtain the desired compound (4.9 g; 3.8 mmol). Yield 95%. The $^{13}$C-NMR, MS and IR spectra were consistent with the given structure.

| Elemental analysis (%): | | | |
|---|---|---|---|
| | C | H | N |
| Calcd. | 71.48 | 9.66 | 6.50 |
| Found | 71.23 | 9.54 | 6.38 |

G) 10-[[2-[2-[2-(Dioctadecylamino)-2-oxoethoxy]-2-oxoethyl]-amino]-2-oxoethyl]-1,4,7,10-tetraazacyclododecane-1,4,7-triacetic acid 10% Pd/C (150 mg) was added to a solution of 10-[[2-[2-[2-(dioctadecylamino)-2-oxoethoxy]-2-oxoethyl]amino]-2-oxoethyl]-1,4,7,10-tetraazacyclododecane-1,4,7-triacetic acid tris(phenylmethyl) ester (1.5 g; 1.2 mmol) in $CH_3COOH$ (150 mL) and the suspension was stirred for 8 h under hydrogen atmosphere at room temperature. After filtration (through a Millipore® filter FT 0.45 μm) the solvent was evaporated and the residue was dried under reduced pressure to give the desired compound (3 g; 1 mmol). Yield 83%. HPLC: 97% (area %). The $^{13}$C-NMR, MS and IR spectra were consistent with the structure.

| Elemental analysis (%): | | | |
|---|---|---|---|
| | C | H | N |
| Calcd. | 65.72 | 10.44 | 8.21 |
| Found | 65.54 | 10.22 | 8.07 |

H) [10-[[2-[2-[2-(Dioctadecylamino)-2-oxoethoxy]-2-oxoethyl]-amino]-2-oxoethyl]-1,4,7,10-tetraazacyclododecane-1,4,7-triacetato(3-)]gadolinium The free ligand from the previous preparation (2.2 g; 2.2 mmol) was dissolved in 3:1 EtOH/$H_2O$ (120 mL); a 0.5 M aq. solution of $(CH_3COO)_3Gd$ (4.4 mL) was added dropwise. The resulting solution was heated at 50° C. for 4 h. The solvent was evaporated to give the title compound (2.2 g; 1.9 mmol). Yield 86%. HPLC: 95% (area %). The MS and IR spectra were consistent with the structure.

| Elemental analysis (%): | | | | |
|---|---|---|---|---|
| | C | H | N | Gd |
| Calcd. | 57.11 | 8.82 | 7.14 | 13.35 |
| Found | 56.98 | 8.74 | 6.98 | 13.23 |

EXAMPLE 18

[10-[1-Methylene-14-octadecyl-2,10,13-trioxo-6,9-dioxa-3,14-diazadotriacontanyl]-1,4,7,10-tetraazacyclododecane-1,4,7-triacetato(3-)] gadolinium

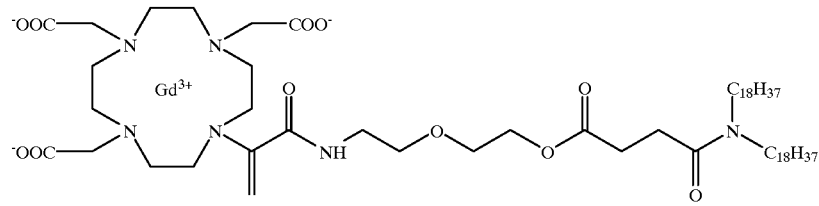

A) 4-(Dioctadecylamino)-4-oxobutanoic acid (C.A.S. Registry No. 37519-63-4)

A suspension of dioctadecylamine (24.5 g; 47 mmol) (prepared according to Example 17, Step A) and succinic anhydride (4.7 g; 47 mmol) in THF (100 mL) was stirred at room temperature for 18 h. Solvent was removed by evaporation and the residue was dissolved in $CH_2Cl_2$. The solution was washed with 1 N HCl, dried and evaporated. The crude was crystallized from $CH_3CN$ to give the desired compound (21.8 g; 35 mmol). Yield 75%. K.F.: 0.37%. The $^{13}C$-NMR, MS and IR spectra were consistent with the structure.

| Elemental analysis (%): | | | | |
|---|---|---|---|---|
| | C | H | N | |
| Calcd. | 77.23 | 12.80 | 2.25 | |
| Found | 77.52 | 13.38 | 2.36 | anhydrous |

B) [10-[1-Methylene-14-octadecyl-2,10,13-trioxo-6,9-dioxa-3,14-diazadotriacontanyl]-1,4,7,10-tetraazacyclododecane-1,4,7-triacetato(3-)]gadolinium 4-(Dioctadecylamino)-4-oxobutanoic acid (7.6 g; 12.3 mmol) in $CHCl_3$ (100 mL) was added to a solution of 10-[2-[[2-(2-hydroxyethoxy)ethyl)amino]-1-(methylene)-2-oxoethyl]-1,4,7,10-tetraazacyclododecane-1,4,7-triacetato(3-)]gadolinium (8.1 g; 12.3 mmol) (prepared according to Example 2 of WO 96/04259) in DMSO (100 mL), then 1-(3-dimethylaminopropyl)-3-ethylcarbodiimmide hydrochloride (EDCI) (2.6 g; 13.4 mmol) and 4-dimethylaminopyridine (DMAP) (0.75 g; 6.1 mmol) were added and the clear solution was stirred at room temperature. After 24 h more EDCI (2.6 g; 13.4 mmol) was added. After another 24 h $CH_3CN$ and $H_2O$ were added to obtain the precipitation of a solid, which was filtered with a paper filter. The solid was dissolved in 1/1 $CH_2Cl_2$/MeOH and the solution loaded onto a silica gel flash column ($CH_2Cl_2$/MeOH=1/1 (v/v) (5 L); $CH_2Cl_2$/MeOH/$H_2O$=5/5/1 (v/v/v) (4 L)). The fractions containing the product were evaporated to give the title compound (6 g; 4.7 mmol). Yield 38%. HPLC: 98% (area %). K.F.: 3.02%. The MS and IR spectra were consistent with the structure.

| Elemental analysis (%): | | | | |
|---|---|---|---|---|
| | C | H | N | Gd |
| Calcd. | 58.06 | 8.87 | 6.66 | 12.46 |
| Found | 58.25 | 8.92 | 6.66 | 12.38 anhydrous |

EXAMPLE 19

[10-[2-[2-(Dioctadecylamino)-2-oxoethoxy]-2-oxoethyl]-1,4,7,10-tetraazacyclododecane-1,4,7-triacetato(3-)]gadolinium

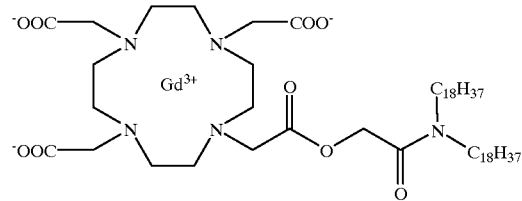

A) 10-[2-[2-(Dioctadecylamino)-2-oxoethoxy]-2-oxoethyl3-1,4,7,10-tetraazacyclododecane-1,4,7-triacetic acid tris-(phenylmethyl) ester DBU (820 μL; 5.5 mmol) was added to a suspension of 1,4,7,10-tetraazacyclododecane-1,4,7,10-tetraacetic acid tris (phenylmethyl) ester (prepared according to Step E3 of Example 17) (3.71 g; 5.5 mmol) in toluene (350 mL) obtaining a clear solution, then 2-bromo-N,N-dioctadecylacetamide (prepared according to Example 5, Step A) (3.9 g; 6.05 mmol) dissolved in toluene (50 mL) was added dropwise. After 2 h the reaction mixture was filtered and the solvent was evaporated. The crude was suspended in $CH_3CN$ (50 mL) and the insoluble was filtered off with a paper filter. The solution was evaporated obtaining the desired product (4.63 g; 3.74 mmol). Yield 68%. The $^{13}C$-NMR, MS and IR spectra were consistent with the structure.

| Elemental analysis (%): | | | |
|---|---|---|---|
| | C | H | N |
| Calcd. | 72.83 | 9.86 | 5.66 |
| Found | 72.67 | 9.58 | 5.71 | anhydrous |

B) 10-[2-[2-(Dioctadecylamino)-2-oxoethoxy]-2-oxoethyl]-1,4,7,10-tetraazacyclododecane-1,4,7-triacetic acid 10% Pd/C (0.4 g) was added to a solution of the product from the previous preparation (4.9 g; 4 mmol) in $CH_3COOH$ (400 mL) and the suspension was stirred for 6 h under hydrogen atmosphere (consumed $H_2$: 270 mL; 12 mmol) at room temperature. After filtration through a Millipore® filter FT 0.45 μm the solvent was evaporated under reduced pressure and the residue was dried (1.3 kPa; NaOH pellets; 35° C.) to give the desired compound (3.1 g; 3.2 mmol). Yield 80%. The $^{13}C$-NMR, MS and IR spectra were consistent with the structure.

| Elemental analysis (%): | | | |
|---|---|---|---|
| | C | H | N |
| Calcd. | 67.11 | 10.74 | 7.25 |
| Found | 67.15 | 10.67 | 7.11 | anhydrous |

C) [10-[2-[2-(Dioctadecylamino)-2-oxoethoxy]-2-oxoethyl]-1,4,7,10-tetraazacyclododecane-1,4,7-triacetato(3-)]gadolinium The free ligand from the previous preparation (3.6 g; 3.7 mmol) was dissolved in 2:1 i-PrOH/$H_2O$ (250 mL) and a 0.5 M aq. solution of $(CH_3COO)_3Gd$ (7.4 mL) was added dropwise. The resulting solution was heated at 50° C. for 6 h. The solvent was evaporated to give the title compound (3.6 g; 3.2 mmol). Yield 87%.

MS and IR spectra were consistent with the structure.

| Elemental analysis (%): | | | | |
|---|---|---|---|---|
| | C | H | N | Gd |
| Calcd. | 57.88 | 8.99 | 6.25 | 14.03 |
| Found | 57.69 | 8.88 | 6.31 | 13.95 | anhydrous |

EXAMPLE 20

10-[2-[Bis[2-[(1-oxohexadecyl)oxy]ethyl]amino]-2-oxoethyl]-1,4,7,10-tetraazacyclododecane-1,4,7-triacetato(3-)]gadolinium A) Hexadecanoic acid iminodi-2,1-ethanediyl ester hydrochloride

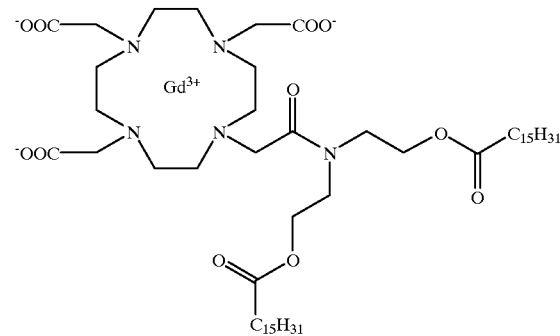

(C.A.S. Registry No. 84454-85-3)

Palmitoyl chloride (29.8 g; 108.4 mmol) (commercial product) was added dropwise in 30 min to a solution of diethanolamine hydrochloride (7 g; 49.4 mmol) (commercial product) in DMF (100 mL). After standing for 1.5 h a white solid crystallized. MeOH (350 mL) was added and the reaction mixture heated to reflux. After cooling to room temperature the recrystallized product was filtered to give as a white solid hexadecanoic acid iminodi-2,1-ethanediyl ester hydrochloride (15 g; 24.2 mmol). Yield 49%. K.F.: 0.4%. The $^{13}C$-NMR, MS and IR spectra were consistent with the structure.

| Elemental analysis (%): | | | | |
|---|---|---|---|---|
| | C | H | N | Cl |
| Calcd. | 69.92 | 11.73 | 2.26 | 5.73 |
| Found | 69.79 | 11.74 | 2.33 | 5.82 | anhydrous |

B) 10-[2-[Bis[2-[(1-oxohexadecyl)oxy]ethyl]amino]-2-oxoethyl]-1,4,7,10-tetraazacyclododecane-1,4,7-triaceticacidtris(phenylmethyl)-ester A 50% solution of 1-propanephosphonic acid cyclic anhydride (14.4 g; 22.6 mmol) in EtOAc (commercial product) was added to a solution of 1,4,7,10-tetraazacyclododecane-1,4,7,10-tetraacetic acid tris(phenylmethyl) ester (15 g; 22.2 mmol) (prepared according to Step E3 of Example 17), hexadecanoic acid iminodi-2,1-ethanediyl ester hydrochloride (14 g; 22.6 mmol) and $Et_3N$ (6.5 mL; 46.6 mmol) in $CH_2Cl_2$ (200 mL). The reaction mixture was stirred at room temperature for 24 h, then more 1-propanephosphonic acid cyclic anhydride (14.4 g; 22.6 mmol) was added. After another 24 h the mixture was washed with brine, dried and evaporated. The residue was purified by flash chromatography ($CH_2Cl_2$/MeOH=9/1 (v/v)) to give the desired compound (17 g; 13.7 mmol). Yield 62%. HPLC: 96% (area %). The $^{13}C$-NMR, MS and IR spectra were consistent with the proposed structure.

| Elemental analysis (%): | | | |
|---|---|---|---|
| | C | H | N |
| Calcd. | 70.78 | 9.36 | 5.65 |
| Found | 70.57 | 9.38 | 5.48 | anhydrous |

C) 10-[2-[Bis[2-[(1-oxohexadecyl)oxy]ethyl]amino]-2-oxoethyl]-1,4,7,10-tetraazacyclododecane-1,4,7-triacetic acid 10% Pd/C (1.6 g) was added to a solution of 10-[2-[bis[2-[(1-oxohexadecyl)oxy]ethyl]amino]-2-oxoethyl]-1,4,7, 10-tetraazacyclo-dodecane-1,4,7-triacetic acid tris (phenylmethyl)ester (16 g; 12.9 mmol) in EtOH (500 mL) and the suspension was stirred for 12 h under hydrogen atmosphere at room temperature. After filtration through a Millipore® filter FT 0.45 μm the solution was evaporated under reduced pressure to give the desired compound. Yield 93%. HPLC: 98% (area %). The $^{13}$C-NMR, MS and IR spectra were consistent with the structure.

| Elemental analysis (%): | | | | |
|---|---|---|---|---|
| | C | H | N | |
| Calcd. | 64.50 | 10.10 | 7.23 | |
| Found | 64.38 | 10.01 | 7.15 | anhydrous |

D) [10-[2-[Bis[2-[(1-oxohexadecyl)oxy]ethyl]amino]-2-oxoethyl]-1,4,7,10-tetraazacyclododecane-1,4,7-triacetato-(3)]gadolinium $(CH_3COO)_3Gd.4H_2O$ (4.63 g; 11.4 mmol) was added to a solution of the free ligand from the previous preparation (11 g; 11.4 mmol) in EtOH (500 mL) at 50° C. After 6 h the solution was evaporated and dried under reduced pressure to give the title compound (12.3 g; 11 mmol). Yield 96%. HPLC: 99% (area %). The MS and IR spectra were consistent with the structure.

| Elemental analysis (%): | | | | |
|---|---|---|---|---|
| | C | H | N | Gd |
| Calcd. | 55.64 | 8.44 | 6.24 | 14.01 |
| Found | 55.57 | 8.41 | 6.12 | 13.92 |

What is claimed is:

1. A compound, either racemic or enantiomeric, of the formulae (†) and corresponding metal chelates:

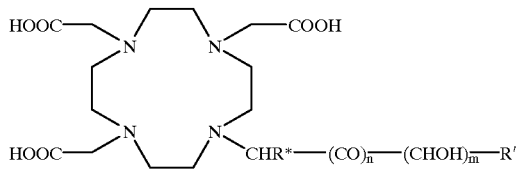

(†)

in which n and m are 1 or 0 but not simultaneously 1, and when n=m=0, R' is H, and R* is a $C_{12-25}$ linear or branched, saturated or unsaturated, hydrocarbon radical;

when n=1 and m=0, R* is H or a $C_{1-3}$ alkyl or alkenyl substituent; and R' is selected from —$NHR_3$, —$NR_4R_5$ and —$OR_6$ where the $R_3$ to $R_6$ are independently $C_{12=}$linear or branched, saturated or unsaturated, hydrocarbon radicals optionally interrupted by —CO— and/or —O— and optionally terminated by —$NR_7R_8$ in which $R_7$ and $R_8$ are independently H or $C_{12-25}$ hydrocarbon radicals; and when n=0 and m=1, R* is H or a $C_{1-3}$ alkyl or alkenyl substituent; and R' is selected from $R_9$ and $CH_2$—O—CO—$R_9$ in which $R_9$ is a $C_{10-30}$ linear or branched, saturated or unsaturated, hydrocarbon radical optionally interrupted by —NH—, —$NR_{10}$—, —CO— or —O—, $R_{10}$ being a lower aliphatic hydrocarbon wherein the metal in the metal chelate is a paramagnetic metal ion selected from Gd(III), Mn(II), Cr(III), Cu(II), Fe(III), Pr(III), Nd(III), Sm(III), Tb(III), Yb(III), Dy(III), Ho(III) and Er(III).

2. A compound of claim 1, having formulae (I), (II) or (III)

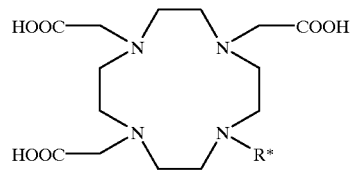

(I)

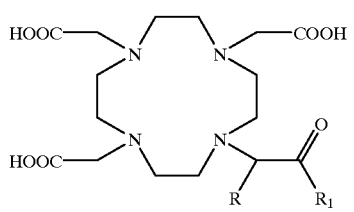

(II)

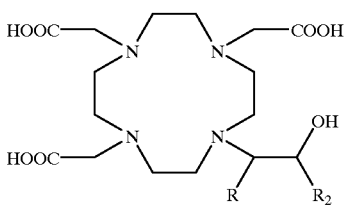

(III)

wherein R* is a $C_{13-26}$ linear or branched, saturated or unsaturated hydrocarbon group;

R is H or a $C_{1-3}$ alkyl or alkenyl substituent;

$R_1$ is selected from —$NHR_3$, —$NR_4R_5$ and —$OR_6$ where the $R_3$ to $R_6$ are independently $C_{12-25}$ linear or branched, saturated or unsaturated, hydrocarbon radicals optionally interrupted by —CO— and/or —O— and optionally terminated by —$NR_7R_8$ in which $R_7$ and $R_8$ are independently H or $C_{12-25}$ hydrocarbon radicals;

$R_2$ is —$CH_2$—O—CO—$R_9$ in which $R_9$ is a $C_{10-30}$ linear or branched, saturated or unsaturated, hydrocarbon radical optionally interrupted by one or more —NH—, —$NR_{10}$—, —CO— or —O—, $R_{10}$ being a lower aliphatic hydrocarbon.

3. A compound according to claim 2 of formula (IIa)

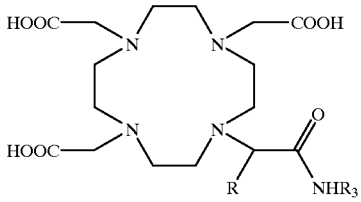

(IIa)

in which $R_3$ is a $C_{12-25}$ linear or branched, saturated or unsaturated, hydrocarbon radical.

4. A compound according to claim 2 of formula (IIb)

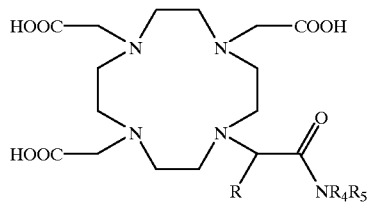

(IIb)

in which $R_4$ and $R_5$ are independently $C_{12-25}$ linear or branched, saturated or unsaturated, hydrocarbon radicals optionally interrupted by —CO— and/or —O—.

5. A compound according to claim 2 of formula (IIc)

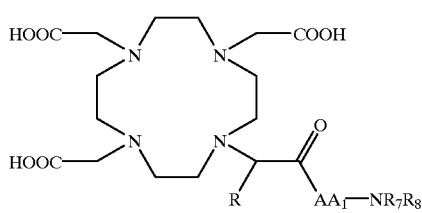

(IIc)

in which A is —NH— or —O—, $A_1$ is a $C_{12-25}$ linear or branched, saturated or unsaturated, hydrocarbon radicals optionally interrupted by —CO— and/or —O—.

6. A compound according to claim 2 of formula (IIIa)

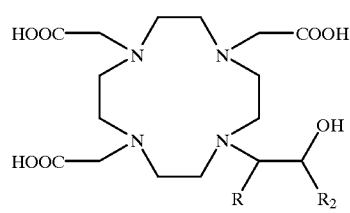

(IIIa)

in which R is H and $R_2$ is a —CH$_2$—O—CO—$R_9$ in which $R_9$ is a $C_{12-25}$ linear or branched, saturated or unsaturated, hydrocarbon radical optionally interrupted by one or more —NH—, —NR$_{10}$—, —CO— or —O— where $R_{10}$ is a lower aliphatic hydrocarbon.

7. A compound according to claim 2 of formula (IIIb)

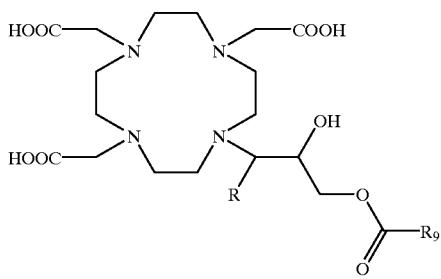

(IIIb)

in which R is H and $R_9$ is a $C_{10-25}$ linear alkyl, or a $C_{10-30}$ linear or branched, saturated or unsaturated, hydrocarbon radical optionally interrupted by one or more —NH—, —NR$_{10}$—, —CO— or —O— where $R_{10}$ is a lower aliphatic hydrocarbon.

8. A compound either racemic or enantiomeric, of the formulae (†) and corresponding metal chelates:

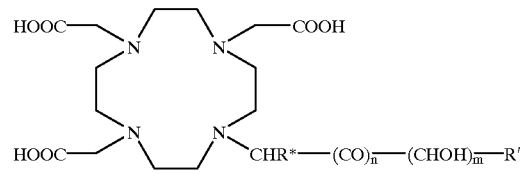

(†)

in which n and m are 1 or 0 but not simultaneously 1, and when n=m=0, R' is H, and R* is a $C_{12-25}$ linear or branched, saturated or unsaturated, hydrocarbon radical;

when n=1 and m=0, R* is H or a $C_{1-3}$ alkyl or alkenyl substituent; and R' is selected from —NHR$_3$, —NR$_4$R$_5$ and —OR$_6$ where the $R_3$ to $R_6$ are independently $C_{12-25}$ linear or branched, saturated or unsaturated, hydrocarbon radicals optionally interrupted by —CO— and/or —O— and optionally terminated by —NR$_7$R$_8$ in which $R_7$ and $R_8$ are independently H or $C_{12-25}$ hydrocarbon radicals; and when n=0 and m=1, R* is H or a $C_{1-3}$ alkyl or alkenyl substituent; and R' is selected from $R_9$ and CH$_2$—O—CO—$R_9$ in which $R_9$ is a $C_{10-30}$ linear or branched, saturated or unsaturated, hydrocarbon radical optionally interrupted by —NH—, —NR$_{10}$—, —CO— or —O—, $R_{10}$ being a lower aliphatic hydrocarbon;

wherein the metal in the metal chelate is a paramagnetic metal ion selected from Gd(III), Mn(II), Cr(III), Cu(II), Fe(III), Pr(III), Nd(III), Sm(III), Tb(III), Yb(III), Dy(III), Ho(III) and Er(III), and wherein said compound is in the form of a complex chelate with paramagnetic metal ions and the salts thereof with physiologically acceptable bases selected from primary-, secondary-, or tertiary amines and basic amino acids, or inorganic hydroxides of sodium, potassium, magnesium, calcium or mixtures thereof;

or with physiologically acceptable anions of organic acids selected from acetate, succinate, citrate, fumarate, maleate, oxalate, or inorganic acids selected from hydrogen halides, sulphates, phosphates, and phosphonates;

or with cations or anions of amino acids selected from lysine, arginine, ornithine, aspartic and glutamic acids.

* * * * *

UNITED STATES PATENT AND TRADEMARK OFFICE
CERTIFICATE OF CORRECTION

PATENT NO. : 6,342,598 B1
DATED : January 29, 2002
INVENTOR(S) : Anelli et al.

It is certified that error appears in the above-identified patent and that said Letters Patent is hereby corrected as shown below:

Column 7,
Line 37, "$Cl_{2-25}$" should read -- $C_{12-25}$ --.

Column 8,
Line 37, "$ME^{n+}$" should read -- $Me^{n+}$ --.

Column 10,
Line 1, "ME" should read -- Me --.

Column 12,
Line 4, "(lic)" should read -- (IIc) --.
First formula, "(A4)" should read -- (a4) --.
Second formula, "(4B)" should be deleted.

Column 14,
First formula, "(A5)" should read -- (a5) --.
Second formula, the "(4B)" under DEPROTECTION should be deleted.
Second formula, "4C" under the formula should read -- 5C --.

Column 18,
Scheme 8, first formula, at the end of "$H_2N$-Chain" insert -- (8B) --.
Scheme 8, third formula, "8C" should changed to -- 8D -- and insert -- $Me^{n+}$ -- at the bottom of the formula but above the newly changed 8D so that the formula looks like the following:

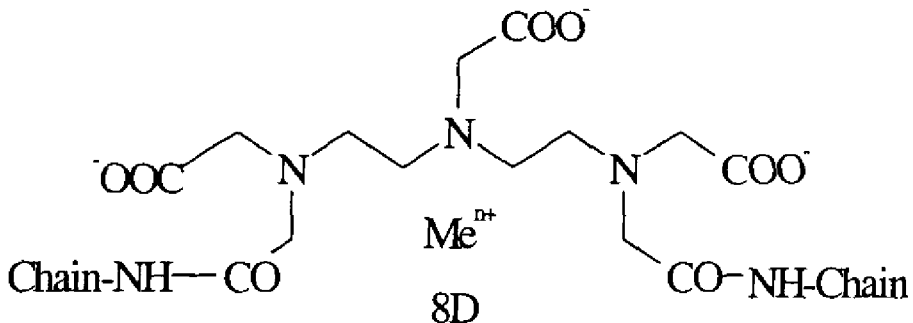

UNITED STATES PATENT AND TRADEMARK OFFICE
CERTIFICATE OF CORRECTION

PATENT NO. : 6,342,598 B1
DATED : January 29, 2002
INVENTOR(S) : Anelli et al.

It is certified that error appears in the above-identified patent and that said Letters Patent is hereby corrected as shown below:

Column 27,
The formula beginning on line 25, has "O" incorrectly placed. The formula should look like the following:

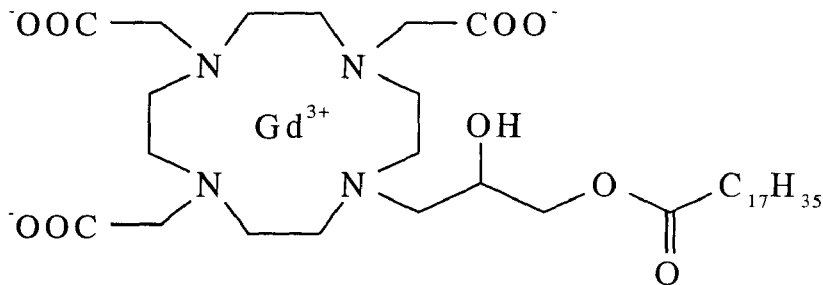

Column 29,
Lines 40-49, the formula, between the two "COO⁻'s" the should be -- $Gd^{3+}$ --.

Column 51,
Line 57, first word should read -- $C_{12-15}$ --.

Signed and Sealed this

Second Day of July, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,342,598 B1
DATED : January 29, 2002
INVENTOR(S) : Anelli et al.

It is certified that error appears in the above-identified patent and that said Letters Patent is hereby corrected as shown below:

Column 7,
Line 37, "$Cl_{2-25}$" should read -- $C_{12-25}$ --.

Column 8,
Line 37, "$ME^{n+}$" should read -- $Me^{n+}$ --.

Column 10,
Line 1, "ME" should read -- Me --.

Column 12,
Line 4, "(lic)" should read -- (IIc) --.
First formula, "(A4)" should read -- (a4) --.
Second formula, "(4B)" should be deleted.

Column 14,
First formula, "(A5)" should read -- (a5) --.
Second formula, the "(4B)" under DEPROTECTION should be deleted.
Second formula, "4C" under the formula should read -- 5C --.

Column 18,
Scheme 8, first formula, at the end of "H₂N-Chain" insert -- (8B) --.
Scheme 8, third formula, "8C" should changed to -- 8D -- and insert -- $Me^{n+}$ -- at the bottom of the formula but above the newly changed 8D so that the formula looks like the following:

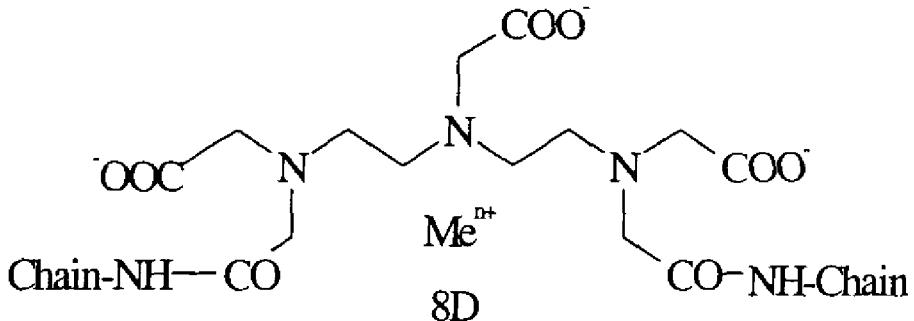

UNITED STATES PATENT AND TRADEMARK OFFICE
CERTIFICATE OF CORRECTION

PATENT NO.    : 6,342,598 B1          Page 2 of 2
DATED         : January 29, 2002
INVENTOR(S)   : Anelli et al.

It is certified that error appears in the above-identified patent and that said Letters Patent is hereby corrected as shown below:

Column 27,
The formula beginning on line 25, has "O" incorrectly placed. The formula should look like the following:

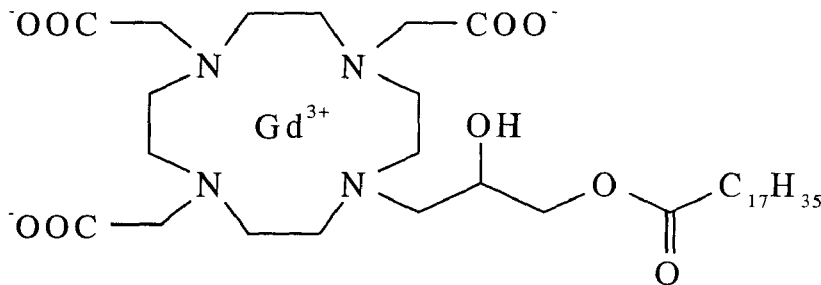

Column 29,
Lines 40-49, the formula, between the two "COO⁻'s" the should be -- $Gd^{3+}$ --.

Column 51,
Line 57, first word should read -- $C_{12-25}$ --.

This certificate supersedes Certificate of Correction issued July 2, 2002.

Signed and Sealed this

Twenty-ninth Day of October, 2002

Attest:

JAMES E. ROGAN
Attesting Officer        Director of the United States Patent and Trademark Office

UNITED STATES PATENT AND TRADEMARK OFFICE
CERTIFICATE OF CORRECTION

PATENT NO.    : 6,342,598 B1
DATED         : January 29, 2002
INVENTOR(S)   : Anelli et al.

It is certified that error appears in the above-identified patent and that said Letters Patent is hereby corrected as shown below:

Column 7,
Line 37, "$Cl_{2-25}$" should read -- $C_{12-25}$ --.

Column 8,
Line 37, "$ME^{n+}$" should read -- $Me^{n+}$ --.

Column 10,
Line 1, "ME" should read -- Me --.

Column 12,
Line 4, "(lic)" should read -- (IIc) --.
First formula, "(A4)" should read -- (a4) --.
Second formula, "(4B)" should be deleted.

Column 14,
First formula, "(A5)" should read -- (a5) --.
Second formula, the "(4B)" under DEPROTECTION should be deleted.
Second formula, "4C" under the formula should read -- 5C --.

Column 18,
Scheme 8, first formula, at the end of "H$_2$N-Chain" insert -- (8B) --.
Scheme 8, third formula, "8C" should changed to -- 8D -- and insert -- $Me^{n+}$ -- at the bottom of the formula but above the newly changed 8D so that the formula looks like the following:

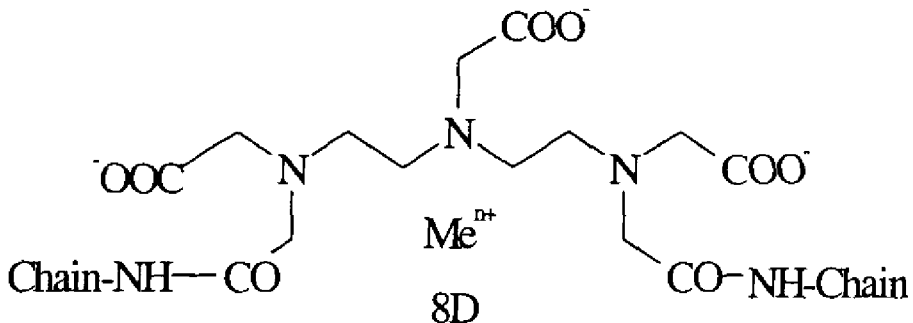

UNITED STATES PATENT AND TRADEMARK OFFICE
CERTIFICATE OF CORRECTION

PATENT NO.   : 6,342,598 B1
DATED        : January 29, 2002
INVENTOR(S)  : Anelli et al.

It is certified that error appears in the above-identified patent and that said Letters Patent is hereby corrected as shown below:

Column 27,
The formula beginning on line 25, has "O" incorrectly placed. The formula should look like the following:

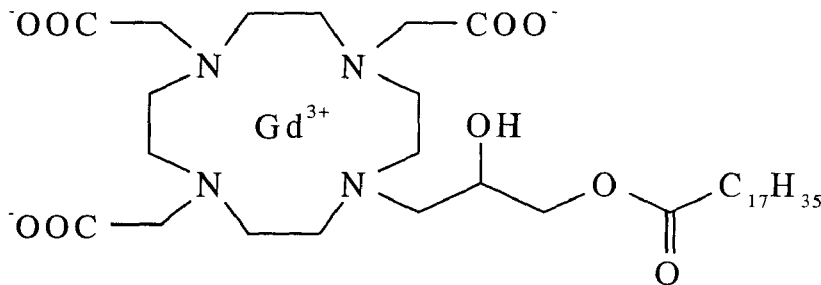

Column 29,
Lines 40-49, the formula, between the two "COO⁻'s" the should be -- $Gd^{3+}$ --.

Column 51,
Line 57, first word should read -- $C_{12-25}$ --.

This certificate supersedes Certificate of Correction issued July 2, 2002.

Signed and Sealed this

Twenty-fourth Day of December, 2002

JAMES E. ROGAN
*Director of the United States Patent and Trademark Office*